United States Patent
Augustine et al.

[19]

[11] Patent Number: 6,070,581
[45] Date of Patent: Jun. 6, 2000

[54] LARYNGEAL AIRWAY DEVICE

[75] Inventors: Scott D. Augustine, Bloomington; Randall C. Arnold, Minnetonka; Thomas W. McGrail, Chaska, all of Minn.

[73] Assignee: Augustine Medical, Inc., Eden Prairie, Minn.

[21] Appl. No.: 08/885,682

[22] Filed: Jun. 30, 1997

Related U.S. Application Data

[63] Continuation-in-part of application No. 08/730,791, Oct. 16, 1996, Pat. No. 5,937,859.

[51] Int. Cl.[7] .................................................. A61M 16/00
[52] U.S. Cl. .............................. 128/207.15; 128/200.26; 623/9
[58] Field of Search .................... 623/9; 604/93, 604/264; 128/207.14, 207.15, 207.16, 200.24, 200.26

[56] References Cited

U.S. PATENT DOCUMENTS

| | | | |
|---|---|---|---|
| 4,351,342 | 9/1982 | Wiita et al. | 128/349 B |
| 4,976,261 | 12/1990 | Gluck | 128/207.14 |
| 4,995,388 | 2/1991 | Brain | 128/207.15 |
| 5,038,766 | 8/1991 | Parker | 128/200.26 |
| 5,259,371 | 11/1993 | Tonrey | 128/200.26 |
| 5,305,743 | 4/1994 | Brain | 128/200.24 |
| 5,443,063 | 8/1995 | Greenberg | 128/207.15 |
| 5,477,851 | 12/1995 | Callaghan et al. | 128/207.15 |
| 5,494,029 | 2/1996 | Lane et al. | 623/9 |
| 5,513,627 | 5/1996 | Flam | 128/200.26 |
| 5,584,290 | 12/1996 | Brain | 128/207.15 |
| 5,623,921 | 4/1997 | Kinsinger et al. | 128/200.26 |
| 5,632,271 | 5/1997 | Brain | 128/207.15 |
| 5,655,528 | 8/1997 | Pagan | 128/207.14 |
| 5,682,880 | 11/1997 | Brain | 128/207.15 |
| 5,743,258 | 4/1998 | Sato et al. | 128/207.15 |
| 5,791,341 | 8/1998 | Bullard | 128/207.15 |

FOREIGN PATENT DOCUMENTS

| | | |
|---|---|---|
| 0 389 272 A2 | 3/1990 | European Pat. Off. . |
| 0 533 371 A2 | 9/1992 | European Pat. Off. . |
| 44 47 186 | 12/1994 | Germany . |
| WO95/32754 | 12/1995 | Japan . |
| 478958 | 1/1938 | United Kingdom .............. 128/207.15 |
| WO 97/12640 | 4/1997 | WIPO . |
| WO 97/12641 | 4/1997 | WIPO . |
| WO 98/50096 | 11/1998 | WIPO .......................... A61M 16/00 |

OTHER PUBLICATIONS

PCT International Search Report for PCT/US97/16838 dated Mar. 13, 1998.

*Primary Examiner*—Michael J. Milano
*Assistant Examiner*—Tram A. Nguyen
*Attorney, Agent, or Firm*—Gray Cary Ware Freidenrich

[57] ABSTRACT

A laryngeal airway device includes an air tube with proximal and distal ends, and a sealing member attached to the distal end of the air tube. The sealing member includes an anterior surface adapted to seat in the throat, against the hyoid bone, and to stretch the laryngeal inlet. A hole extends through the anterior surface and the sealing member and communicates through an air passage with the distal end of the air tube. When the sealing member is seated in the throat, the hole is contained within the rim of the stretched laryngeal inlet, with which the anterior surface forms a seal that surrounds the hole. Airway patency is thereby ensured.

36 Claims, 26 Drawing Sheets

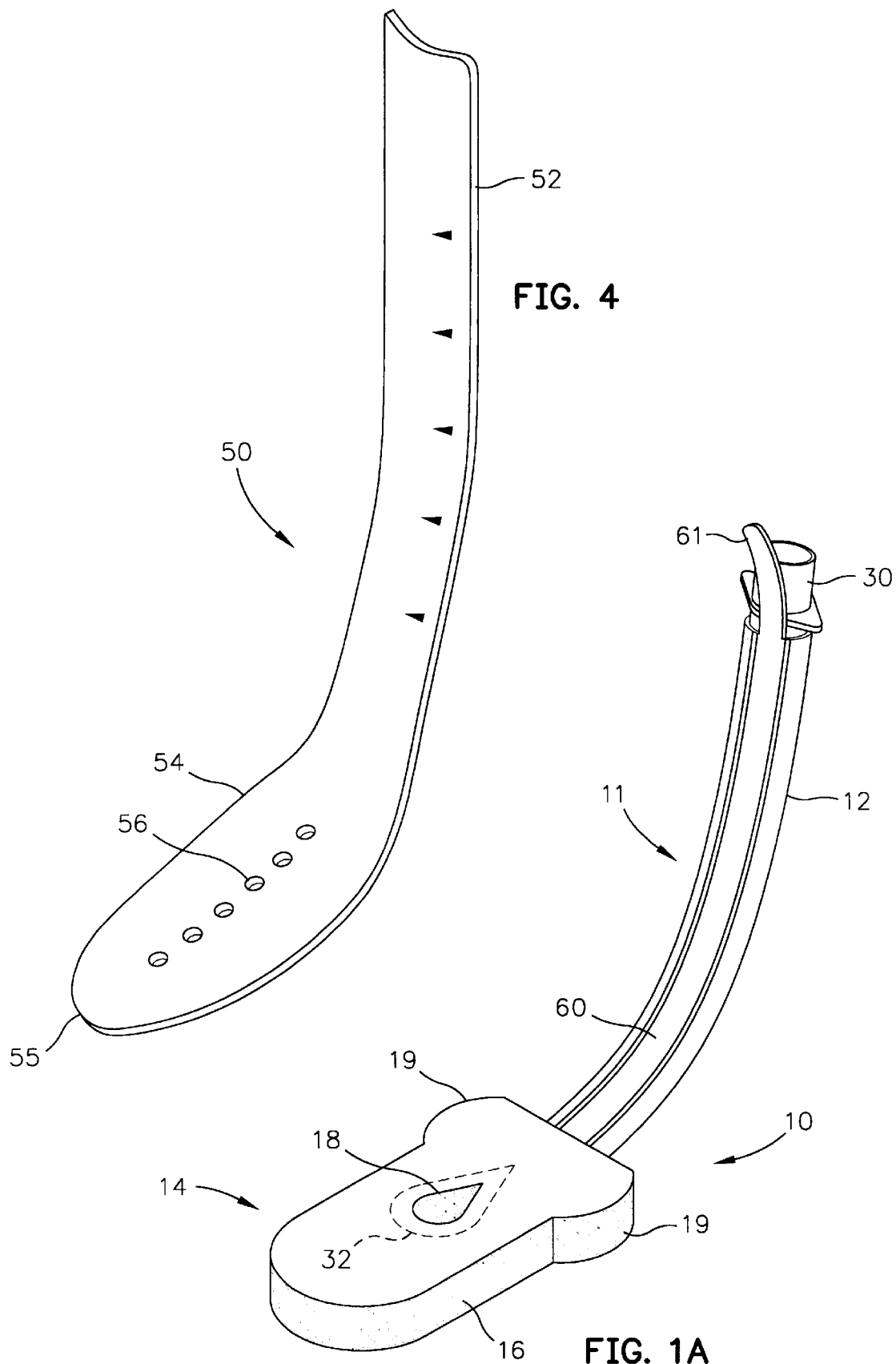

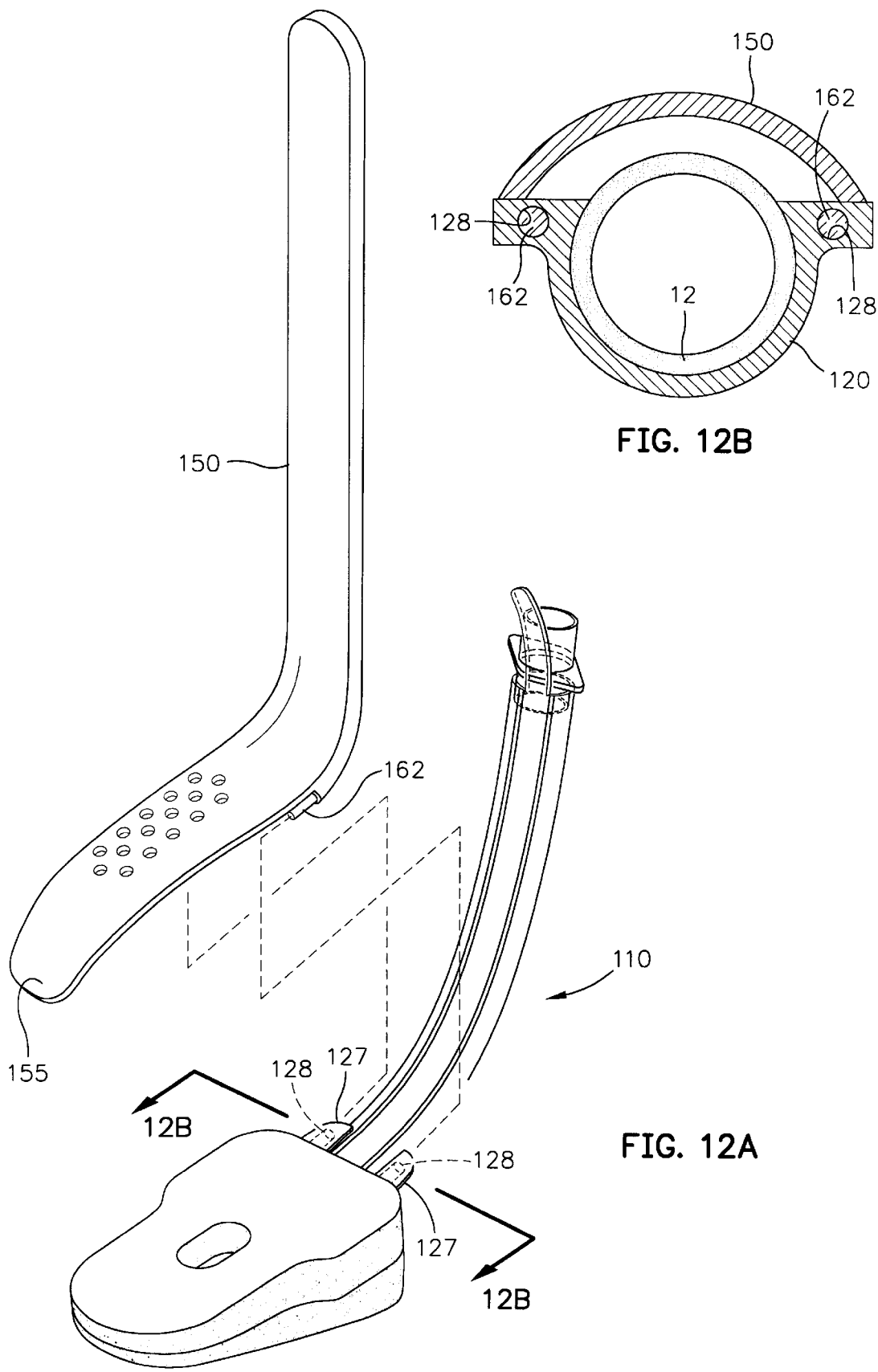

LARYNGEAL AIRWAY DEVICE

CROSS REFERENCE TO RELATED APPLICATIONS

This is a continuation-in-part of U.S. patent application Ser. No. 08/730,791, filed Oct. 16, 1996, now U.S. Pat. No. 5,937,859, for LARYNGEAL AIRWAY DEVICE.

BACKGROUND OF THE INVENTION

1. Field of the Invention

This invention is concerned with the management of a human airway in order to control respiration. More particularly, the invention concerns a device that couples an airway tube reliably and safely with the laryngeal opening, the upper end of the trachea, which is the breathing passageway that leads to the lungs. The device seats in the throat immediately adjacent the laryngeal opening, tensions and erects the laryngeal opening, and seals within the laryngeal opening to provide a channel through the airway tube for artificial ventilation of the lungs.

2. Prior Art

The airway of a human being includes the throat and windpipe, and leads to the lungs. Control and management of a patient's airway are required under a variety of circumstances. During the administration of general anesthesia, in particular, the resultant loss of consciousness and muscle tone require that patient ventilation be maintained through an artificial airway. Control of a patient's airway is also necessary to permit mechanical ventilation of a patient with diseased or injured lungs and during resuscitation of a hemodynamically compromised and apneic or non-breathing patient. Mechanical ventilation of a patient involves forming a seal about some portion of the patient's breathing anatomy and introducing air that varies in pressure through the seal. The air is provided through a tube from a ventilating machine. The seal confines the varying air pressure in the airway and lungs of the patient, imposing an artificial respiration on the lungs. A breach in the seal undesirably lets the varying pressure escape to the ambient atmosphere, which inhibits airway management. Therefore, the quality and efficacy of an airway management device depends upon the seal that it forms where it interfaces with a patient's airway.

A wide variety of devices are currently available to manage a patient's airway. For simplicity, these airway devices can be categorized as follows: face masks, tracheal tubes and pharyngeal airways.

A face mask covering the mouth and nose and with a port for connection to a ventilation means is commonly used for short term control of the airway. The face mask is non-invasive in that sealing of the airway is accomplished not by penetration into the patient's airway, but rather by skin contact, with the mask encircling the mouth and nose. However, airway patency is not assured since the tongue and other structures can obstruct the airway. Also, it is difficult to maintain a seal of the airway for any period of time, particularly during positive pressure ventilation. Leakage around the face mask results in ineffective ventilation and, during anesthesia, contaminates the operating room with anesthetic gases. Furthermore, a face mask does not prevent the introduction of air into the esophagus and stomach (gastric insufflation) or protect against the aspiration of stomach contents (breathing of vomited material). Still further, the face mask precludes surgical field avoidance during oral, nasal and facial procedures, and it is inappropriate for patients with facial burns.

Tracheal tubes (also called endotracheal tubes and ETTs) are inserted through the mouth or nose and into the trachea (the windpipe) where an inflatable balloon or cuff surrounding the tube seals against the interior surface of the trachea. This approach avoids the deficiencies of face masks because it includes the provision of a conduit traversing the pharynx, and forms an effective seal against the airway, allowing positive pressure ventilation, and protection against aspiration of stomach contents. However, while solving several problems, tracheal tubes create new challenges. They are difficult to insert and position properly within the trachea, almost always requiring a laryngoscope, stylet or other intubation aid. Penetration of the larynx and trachea is invasive and is a highly noxious stimulus requiring a deep plane of anesthesia. Furthermore, once in place, tracheal tubes injure the delicate tissue of the larynx and trachea including the vocal cords. Incorrect positioning of the tube tip (distally into the mainstem bronchi or proximal dislocation out of the trachea) is an additional concern.

Another method of ensuring a patent airway is to insert a tracheostomy tube through an opening in the front of the neck and directly into the trachea. This approach is even more invasive than the tracheal tube in that it requires surgery to install the tube; consequently, it is reserved for patients chronically requiring ventilatory assistance or for those needing emergency relief from an obstructed upper airway.

With the current trend toward minimally invasive surgery, the concept of an airway management device with a supra-glottic seal without the stimuli of tracheal intubation has widespread appeal. A supraglottic seal seals in the throat, above the larynx, while providing a passageway to the laryngeal opening through which ventilatory gases may be delivered. Since these devices normally terminate in the pharynx, the portion of the throat from the mouth to the larynx, they are commonly referred to as "pharyngeal" devices. When combined with a breathing tube, a pharyngeal device is called a "pharyngeal airway" device.

A variety of pharyngeal airway devices have been developed for assistance in maintaining a human airway. Some oro-pharyngeal airway devices are useful in displacing the tongue or as bite blocks, but are incapable of maintaining the airway by themselves, since a seal is not effected. Other devices include a tube with a cuff to seal against the pharyngeal wall at the base of the tongue, and with another cuff that seals around the plugged distal end of a tube situated in the esophagus. Patient ventilation occurs through side holes in the tube between the two cuffs, the side holes aligned with the laryngeal opening.

Another pharyngeal airway device includes a tube with an inflatable cuff surrounding its distal end. The cuff is intended to seal against the pharyngeal wall, above the epiglottis.

Generally, pharyngeal airway devices seal against pharyngeal structures surrounding the larynx, and merely mask or cover the larynx, rather than sealing within or directly against it. These devices characteristically form inadequate seals that leak with a moderate level of positive pressure ventilation. Further, these devices provide easily breached or imperfect barriers between the esophagus and trachea, allowing gastric insufflation and/or aspiration of stomach contents. Also, these devices usually include air channels with small bores that limit the size of tracheal tubes that can be inserted into a trachea, should intubation be desired.

The inadequate sealing performance of pharyngeal airway devices is not surprising considering their designs and the anatomy with which they interface. The larynx ("voice box") is the most proximal part of the trachea and opens into the pharynx, immediately behind the base of the tongue. The adult laryngeal inlet (the opening into the larynx and trachea) looks very similar to a piece of pipe, approximately ⅝" in diameter with its end beveled at an approximately 30° angle. The pipe analogy is accurate when describing the general appearance of the trachea and larynx, however it is not an accurate analogy of the functional anatomy. The laryngeal inlet is not a rigid structure. The anterior wall of the laryngeal inlet (the side facing the tongue), including the tip of the beveled end of the inlet, is formed by the epiglottis, which is a flexible cartilage. The epiglottis provides some structure to the laryngeal inlet but is sufficiently flexible that it can easily be bent posteriorly, away from the tongue, to fully cover and block the inlet. The distal posterior aspect of the laryngeal inlet is formed by two small, movable arytenoid cartilages. Finally, the side walls of the laryngeal inlet are formed by very flexible quadrangular membranes attached to the arytenoid cartilages posteriorly and to the epiglottis anteriorly. The proximal edges of the quadrangular membranes become the aryepiglottic folds that form the rim of the laryngeal inlet. It is obvious that this combination of flexible cartilages and membranes creates an inlet to the airway that is structurally strong with respect to tension and stretching, but that has virtually no structural strength with respect to compression. Radially compressive forces applied to the laryngeal inlet will easily collapse the inlet into itself, thereby covering and blocking the airway. Manifestly, radially compressive forces could not possibly form a seal against the compressible laryngeal inlet.

SUMMARY OF NEED

There is a need for an airway management device with the following attributes:

non-invasive and supraglottic (does not contact structures below the vocal cords),
  seals directly within the laryngeal inlet instead of against the pharyngeal structures,
  makes a seal that is sufficient to permit positive pressure ventilation,
  avoids gastric insufflation and aspiration,
  is easy to insert,
  provides definitive endpoint of insertion that ensures alignment with the airway opening and remains seated in that position,
  makes a nontraumatic seal of airway,
  employs simple, cost-effective design permitting single use, and
  passes an adult sized ETT through its air channel to facilitate optional intubation of the trachea.

SUMMARY OF THE INVENTION

Our invention is a laryngeal airway device comprising a curved or flexible tube with proximal and distal ends. The tube has a sealing member attached at its distal end that forms a seal within the rim of the laryngeal inlet. The seal within the rim of the laryngeal inlet makes our device fundamentally different than pharyngeal airway devices which seal against pharyngeal structures. Substantially in the midline of the anterior surface of the sealing member is a hole in communication with the distal end of the flexible tube. The hole approximates the aperture of the laryngeal inlet when the device is properly positioned for use, forming an air conduit with the larynx.

As previously discussed, the cartilaginous support structure and membranous side walls of the laryngeal inlet are both compressible and collapsible and are therefore difficult to seal against. Our device seals against the compressible and collapsible laryngeal inlet in a very specific and unique way. Our key observation is that while the laryngeal inlet may have little strength to resist external circumferential compression, it has considerable tensile strength (the ability to resist stretching). We have also observed that the epiglottic cartilage forming the anterior wall of the laryngeal inlet is attached to the thyroid cartilage of the larynx at its distal end and at its proximal end is free to move in an anterior or posterior direction, like a "lever". Attached to and supported by this "lever" are the flexible quadrangular membranes which form the side walls of the laryngeal inlet. The proximal edge of the quadrangular membranes, called the ary-epiglottic folds, form the majority of the rim of the laryngeal inlet. Pivoting the epiglottic "lever" in an anterior direction (toward the tongue) stretches the ary-epiglottic folds between the epiglottis and their posterior attachment on the arytenoid cartilages. The ary-epiglottic folds are minimally stretchable and, when tensioned, create a relatively firm rim at the laryngeal inlet. The pad of our device abuts and seals against and within the tensioned rim of the laryngeal inlet.

The critical features of our novel device are;

1.) when seated, it erects and tensions the rim of the laryngeal inlet by pivoting the epiglottic "lever" anteriorly to stretch the ary-epiglottic folds, creating a relatively firm rim to seal against, and
  2.) it has a sealing member which closely abuts and engages the now-tensioned rim of the laryngeal inlet, creating a seal.

Accordingly, it is an object of this invention to provide a laryngeal airway device with which a human airway may be managed.

Another object of this invention is the provision of an airway device with which a human airway may be managed by formation of a seal between the device and the laryngeal opening.

Yet another object of this invention is the provision of a laryngeal airway device that tensions the rim of the laryngeal inlet with which it then forms a seal for airway management.

Yet another object of this invention is the provision of airway management by means of a laryngeal device that seals against the compressible and collapsible laryngeal inlet.

These and other objects, advantages, features, and functions of our invention will become apparent from the following detailed description when read in conjunction with the below-described drawings.

BRIEF DESCRIPTION OF THE DRAWINGS

FIG. 1A is a perspective view of a first embodiment of the laryngeal airway device of the invention, when assembled;

FIG. 4 is perspective view of a pharyngeal blade optionally used with the first embodiment;

FIGS. 12A and 12B illustrate an alternative optional means for retaining an optional pharyngeal blade on the laryngeal air device.

DETAILED DESCRIPTION OF THE PREFERRED AND ALTERNATE EMBODIMENTS

Figure 1B:
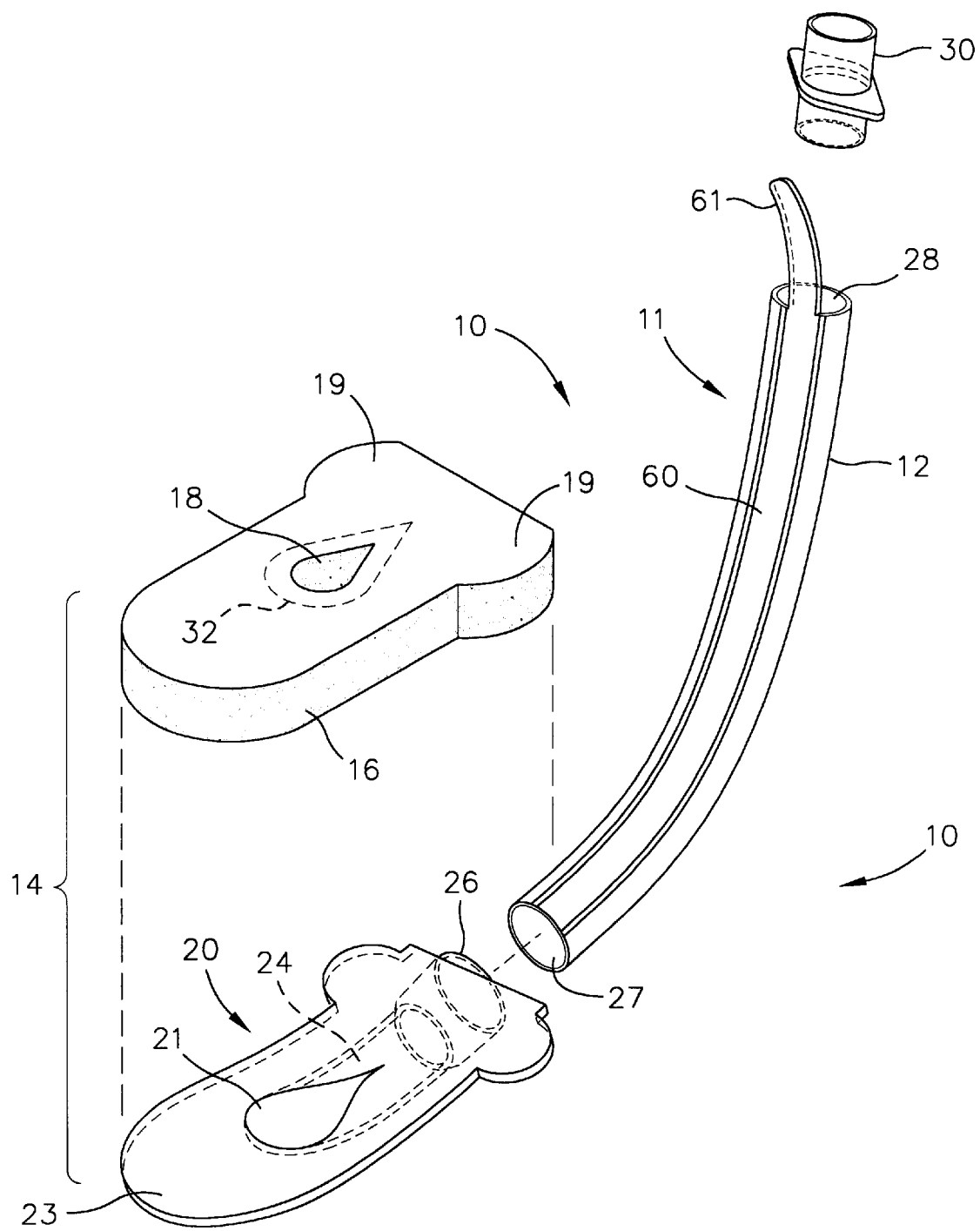
FIG. 1B is an exploded perspective view of the first embodiment.
Figure 1C:
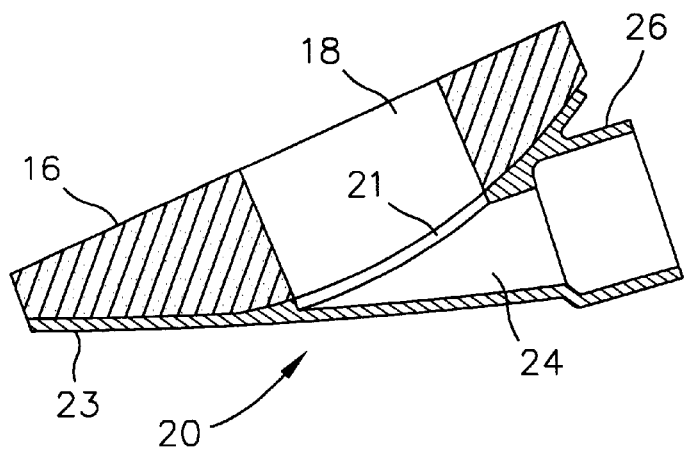
FIG. 1C is a side sectional illustration of a support member of the first embodiment.

Referring now to the drawings, in which like reference numerals indicate the same parts throughout, FIGS. 1A, 1B and 1C illustrate one embodiment of our invention. The first embodiment of our invention is a laryngeal airway device 10 that includes an air channel 11 and a sealing member 14. The primary component of the air channel 11 is an air tube 12. The sealing member 14 includes a pad 16 of soft, compliant material, having a hole 18. The hole 18 opens through the pad 16. The sealing member 14 further includes a wedge-shaped molded plastic support member 20 having a passageway 24 that transitions to a socket 26 in its rearward end. The socket 26 accepts the distal end 27 of the air tube 12. The passageway 24 opens through the support member 20 by way of a hole 21 that aligns with the hole 18 in the pad 16. Mounted to the proximal end 28 of the air tube 12 is a connector 30. The laryngeal airway device 10 as thus far described, is assembled by suitably bonding the air tube 12, pad 16, and support member 20 together. For example, with the distal end 27 of the air tube 12 glued into the socket 26 of the passageway 24, the posterior surface of the pad 16 can be glued to the anterior surface 23 of the support member 20. Thus assembled, the air channel 11 provides an air pathway that is open from the proximal end 28 of the air tube 12 through the tube 12, the support member passageway 24, and the hole 18 in the pad 16. With connection of a ventilating device to the connector 30, controlled, artificial respiration can be provided when the laryngeal airway device 10 is seated in the throat of a person, as will be described further.

The pad 16 (also, "conformable cushion") forms the anterior face of the sealing member 14 of the laryngeal airway device 10. The pad 16 is adapted to abut against and conform to the rim of the laryngeal opening (as opposed to surrounding it) to form a seal therewith. Assuming that the dotted line 32 represents the outline of the rim of the laryngeal inlet where it contacts the pad 16, one can see that the hole 18 is contained within that rim. Application of a seating force on the sealing member 14 in the direction of the rim of the laryngeal opening will cause the portion of the pad 16 that abuts the laryngeal opening rim at 32 to compress against the rim. Pad material between the hole 18 and the rim of the laryngeal opening at 32 will be uncompressed, as will material between the rim of the laryngeal opening and the outside edge of the pad 16. This forms an effective seal between the laryngeal opening and the pad 16 that constrains artificial ventilation delivered by way of the hole 18 to the airway and lungs of a patient.

The pad 16 is preferably made of a closed-cell polyvinyl chloride (PVC) foam material, or equivalent. The slow time required by certain closed-cell foams to re-expand after compression may be advantageous in our invention. Some of these foams remain compressed for 15–45 seconds after release of a compressive force. This characteristic of the foam material allows time for the laryngeal airway device 10 to be inserted into a patient's mouth with the pad compressed, reducing the anterior-posterior thickness of the pad 16 and its total bulk. After a short delay, the resilient foam re-expands to its total thickness, remaining compressed only against the rim of the laryngeal opening at 32 to advantageously form a seal with the larynx. Many other open or closed foam cell materials are also suitable, with or without surface "skinning". The pad 16 may alternatively be made from any other suitable compressible and resilient material, or from an inflatable bladder.

The laryngeal airway device in which the pad 16 is formed of a foam material may have an additional advantage. The foam may absorb fluids with which it comes into contact. Preapplication of fluids to the pad 16 before insertion is expected to improve the sealing capability of the pad 16 against the rim of the laryngeal inlet. The natural saliva in the pharynx is also expected to improve the seal.

The upper surface of the pad 16 forms the anterior surface of the laryngeal airway device. This surface may be contoured in manner that is adapted to the contour of the throat in the vicinity of the laryngeal inlet. One example of a contoured pad 16 may include a slight anterior projection of the anterior face of the cushion in the area immediately proximal to the hole 18. This projection is expected to force the epiglottis anteriorly, to assist in tensioning the rim of the laryngeal inlet. Alternatively, the anterior surface of the pad 16 may be substantially planar.

The hole 18 (of which there may be one or more) is substantially in the midline of the anterior face of the pad 16 and is in communication with the distal end 27 of the air tube 12 on the posterior side of the pad 16. The hole 18 provides a conduit for delivering ventilatory gases from the distal end 27 to the laryngeal inlet. Preferably, there is a single hole 18 whose transverse dimension is smaller than the corresponding transverse diameter of the laryngeal inlet, thereby allowing the material of the pad 16 surrounding the hole to form a seal by abutting against the rim of the laryngeal inlet as described above. Importantly, in forming the seal, some of the material of the pad 16 intrudes into or penetrates the larynx and is within the laryngeal inlet when the pad 16 abuts the rim at 32. Preferably, the hole 18 is elongate in shape, narrowest in its transverse dimension. Further preferably, the hole 18 has an elongate teardrop shape, with its pointed end directed proximally. Considering the oval shape of the rim of the laryngeal inlet at 32, the elongate teardrop-shaped hole 18 in the pad 16 maximizes the chances of alignment and patency along the longitudinal axis, the axis with the highest chance of error in alignment. The narrow portion of the hole 18 prevents the epiglottis from falling into and occluding the air channel formed by the hole 18 in the pad 16, while still providing the maximal opportunity for longitudinal alignment.

Figure 2A:
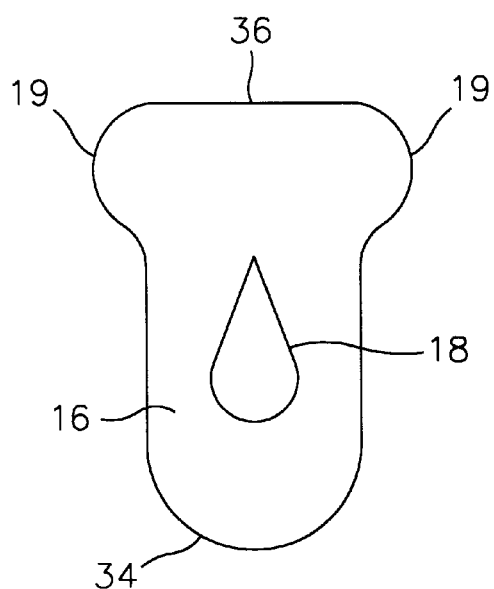
FIGS. 2A and 2B are respective top views of pad configurations used on a sealing member of the first embodiment.
Figure 2B:
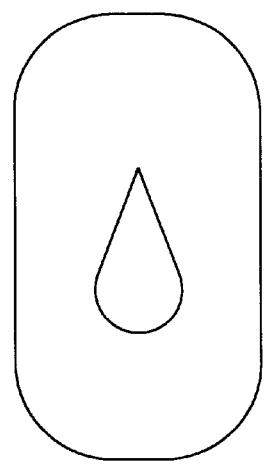

Referring now to FIGS. 2A and 2B, the pad 16 is illustrated, in top plan, in FIG. 2A. The periphery of the pad 16 has a quasi-rectangular shape with a rounded distal end 34. The distal end 34 of the pad 16 seats in the hypopharyngeal space, just above the upper esophageal sphincter. As opposed to the typical pharyngeal airway device, our laryngeal airway device is not intended to enter the upper esophagus. To aid in providing a stop point for accurate insertion depth, the two small lateral protrusions or wings 19 are formed on either side of the proximal end 36 of the pad 16. An alternative embodiment of the pad 16 is illustrated in FIG. 2B. This embodiment comprises a substantially rectangular periphery with rounded corners.

Figure 3:
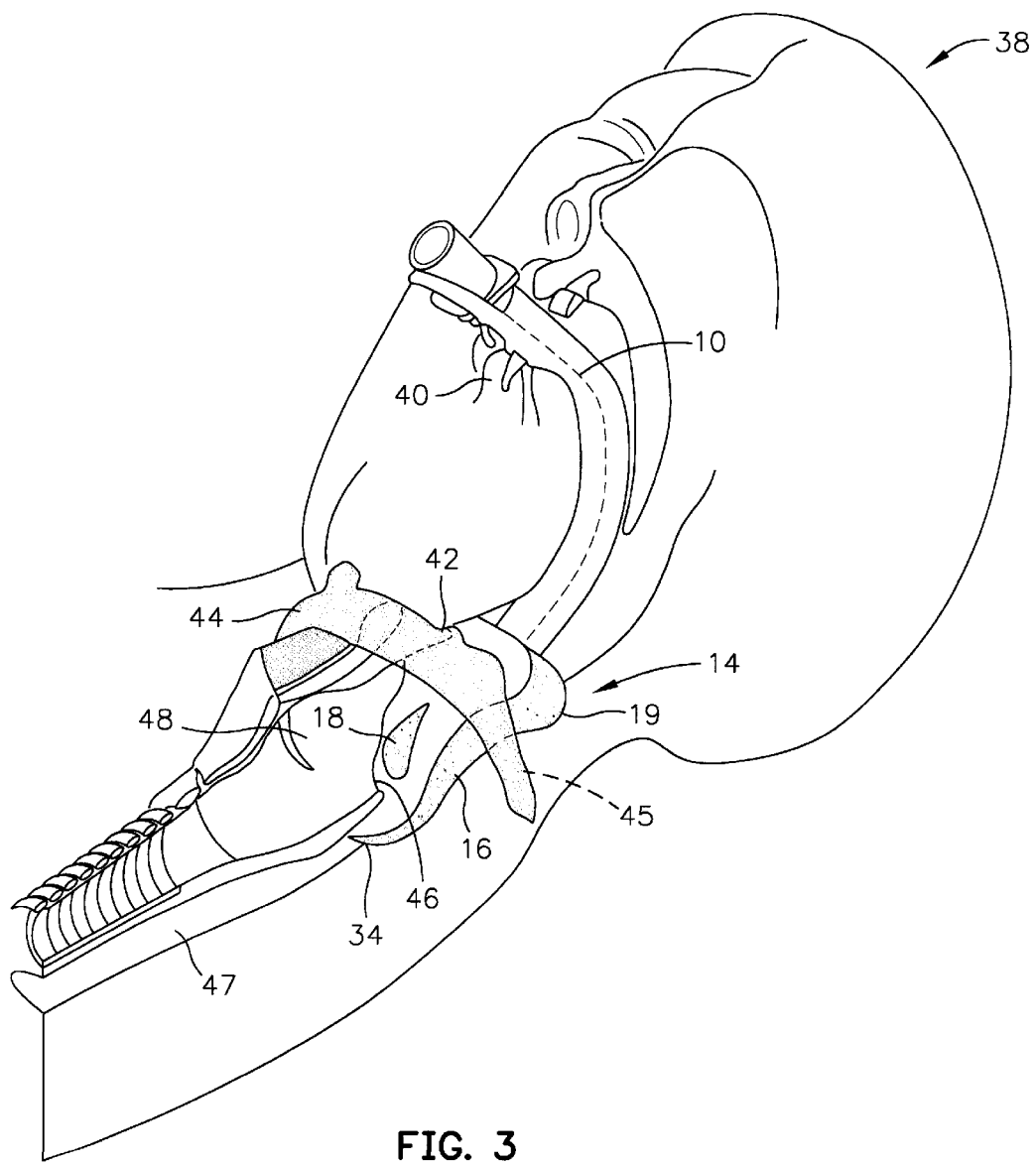
FIG. 3 is a partial cutaway view of the head and throat of a patient showing how the first embodiment of the laryngeal airway device seats in the throat.

With reference now to FIG. 3 and to the illustrated embodiment, we will describe how the laryngeal airway device 10 embodies the critical features set forth in the Summary of the Invention. In FIG. 3, the upper portion of a patient 38 is shown in a partially schematic, partially cutout view with our laryngeal airway device 10 inserted through the patient's mouth 40. The illustrated portion of the patient's anatomy includes the epiglottis 42, and hyoid bone 44. The laryngeal inlet comprises the aryepiglottic fold 46 whose upper edge forms a portion of the rim of the laryngeal opening that abuts the pad 16 at the position indicated by reference numeral 32 in FIGS. 1A and 1B. The upper portion of the airway, immediately within the rim of the laryngeal opening is referred to as the laryngeal vestibule 48.

We have observed that the hyoid bone 44 is attached to the epiglottis 42 in its midline by the hyo-epiglottic ligament. When the patient 38 is standing upright, the U-shaped hyoid bone 44 is substantially horizontally oriented. The hyoid bone 44 is always positioned in the airway at the level of the laryngeal inlet. The side portions of the U-shaped of the hyoid bone are referred to as the greater horns. One greater horn 45 is visible in dotted outline in FIG. 3. The greater horns of the hyoid bone 44 define the transverse width of the pharynx at the level of the laryngeal inlet. The shape of the periphery of the pad 16 is adapted to fit transversely between the greater horns of the hyoid bone 44. Lateral alignment between the pad 16 and the laryngeal inlet rim is assured by the transverse dimension which adapts the pad to fit snugly between the greater horns of the hyoid bone 44. In the "winged" embodiment of the pad 16, the laterally protruding wings 19 are adapted to be wider than the transverse width between the greater horns of the hyoid bone 44. During insertion, the laryngeal airway device 10 is advanced into the pharynx, sealing member first, until the lateral protruding wings 19 contact and seat on the greater horns of the hyoid bone 44, preventing further advancement. Since the hyoid bone 44 is always at the level of the laryngeal inlet, the winged shape of the sealing member 14 provides a positive endpoint, assuring dependable longitudinal alignment between the hole 18 and the laryngeal inlet.

When the wings 19 of the pad 16 are properly seated on the hyoid bone 44, the wings also help to prevent the laryngeal airway device from accidental dislodgment. The wings 19 in effect are trapped between the hyoid bone 44 distally and the soft tissue of the tonsillar pillars (not shown) proximally, which are located on the side walls of the pharynx near the back of the throat. The tonsillar pillars create a resistance to spontaneous ejection of the airway device from its properly seated position.

Returning to FIGS. 1A, 1B and 1C, in a longitudinal section, the sealing member 14 is substantially wedge shaped, to approximate the angle of the bevel of the laryngeal inlet. The distal end of the sealing member 14 is thin in the antero-posterior dimension, while the proximal portion is thicker. As shown in FIG. 1C, the support member 20 is preferably made of a molded flexible plastic which is stiffer than the material of which the pad 16 is made, yet which is pliable enough to aid in the insertion of an endotracheal tube (described below). The support member 20 serves to anchor the distal end 27 of the air tube 12. Preferably, the passageway 24 of the support member is a complete conical, or cylindrical space with the hole 21 in its anterior wall.

The air tube 12 is preferably a curved or flexible tube made of PVC or urethane plastic. Alternatively, other types of plastic and rubber material would also be suitable.

Referring now to FIG. 4, an optional pharyngeal blade 50 facilitates insertion of the laryngeal airway device 10, and eliminates the need for a clinician to insert fingers in the throat and mouth of the patient. The pharyngeal blade 50 is substantially J-shaped, with the upper leg 52 of the J serving as a handle and the lower leg 54 of the J acting as an insertion blade. Preferably, the lower leg 54 widens and then narrows to the distal tip 55 to present a spoon-like shape. There are one or more holes 56 through the lower leg 54 that permit ventilation through the laryngeal inlet when the blade is used. Alternatively, the blade may be substantially L-shaped. The blade 50 is preferably constructed of a lightweight, relatively stiff plastic such as polypropylene or PVC. Alternately, the blade 50 may be made of metal, or other suitable materials.

Figure 5A:
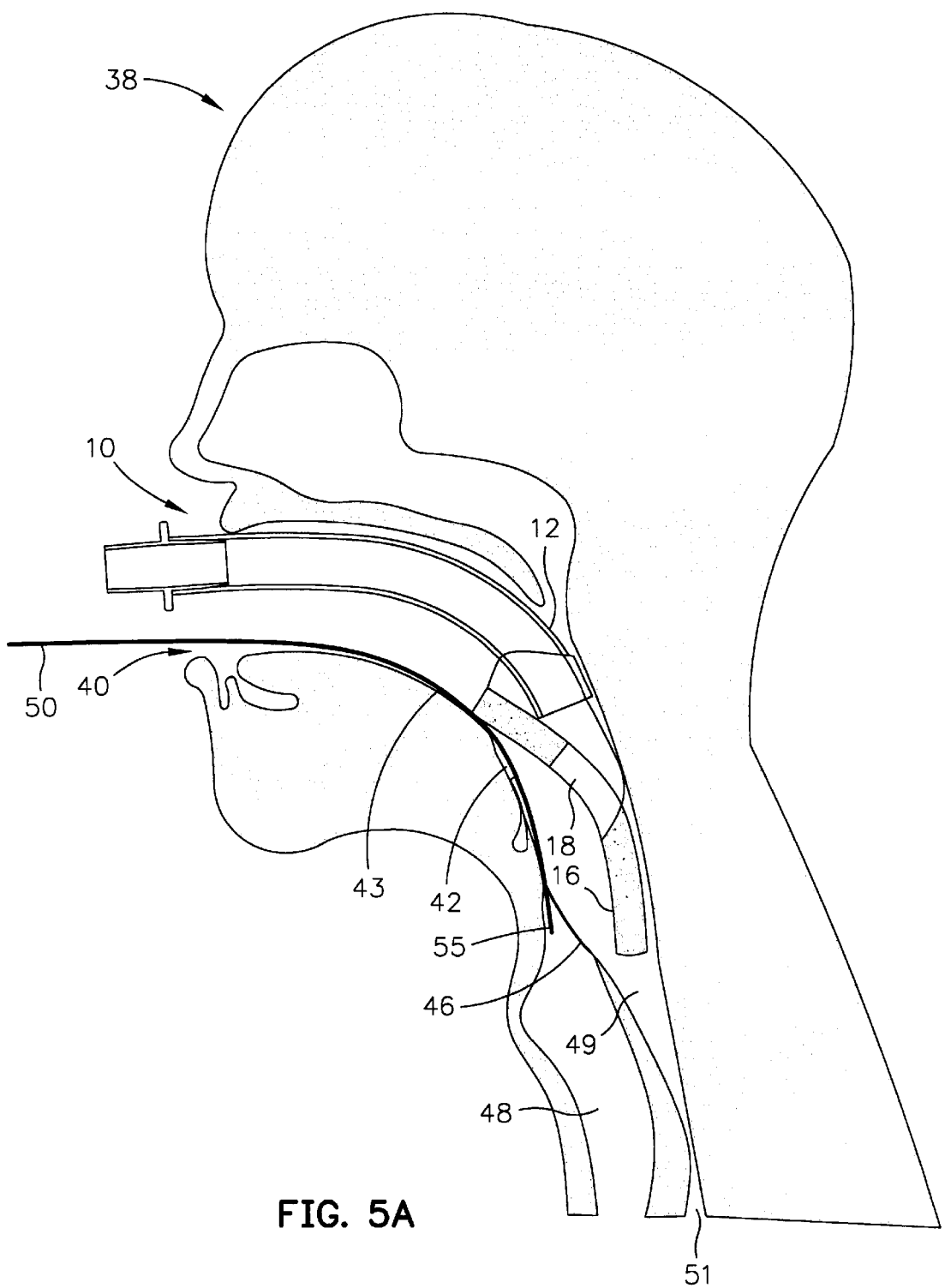
FIGS. 5A–5C illustrate a side sectional view of the anatomy of a human airway in which the first embodiment is inserted and seated for use.
Figure 5B:
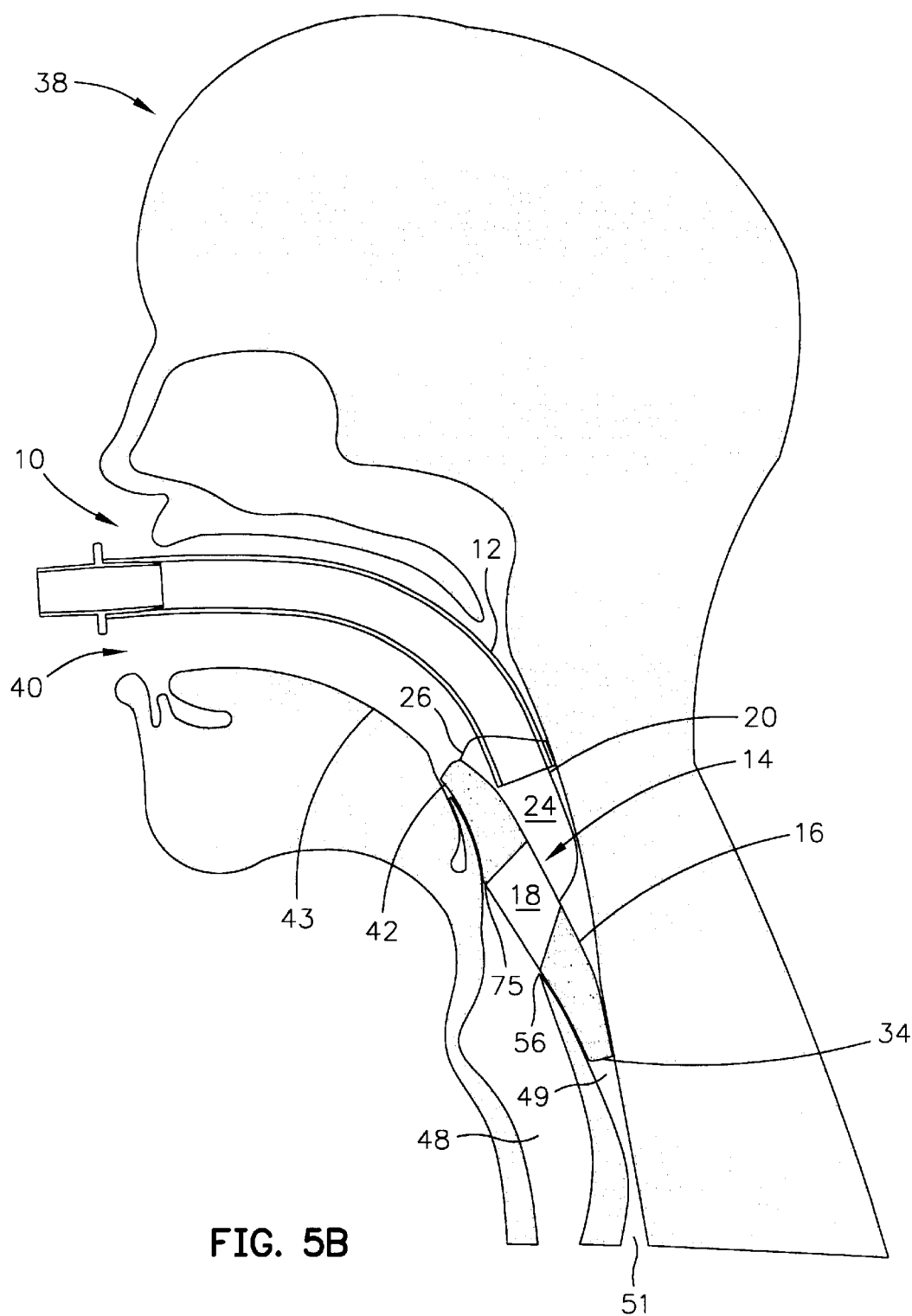

Use of a laryngeal airway device according to the invention is illustrated in FIGS. 5A and 5B. These pictures are side views showing a side elevation section of the head and throat of the patient 38 illustrated earlier in FIG. 3. In use, if the pharyngeal blade 50 is employed, the blade 50 is directed to the back of the pharynx of the patient 38 and, when the distal tip 55 of the blade contacts the posterior pharyngeal wall, the blade 50 is then pivoted as it is advanced caudally down the throat. The smooth blade surface elevates the epiglottis 42 anteriorly and slides along the tongue 43 and epiglottis 42, without allowing either of these flexible structures to fold over the laryngeal inlet. When the blade 50 is fully inserted into the pharynx, the blade 50 is lifted in an antero-caudad direction to open the mouth 40 and retract the tongue 43, creating an open channel for the laryngeal airway device 10. The holes 56 permit ventilation through the laryngeal inlet. The laryngeal airway device 10 is then introduced through the mouth 40, advancing it along the posterior surface of the blade 50 until it meets a resistance to further advancement. At this point the wings 19 of the preferred embodiment have engaged the greater horns of the hyoid bone (not shown in FIGS. 5A–5C) as discussed above, and the hole 18 is in proper alignment with the laryngeal inlet. The blade 50 is then removed by simply pulling it out of the mouth 40, while holding the proximal end of the air tube 12 to stabilize the laryngeal airway device 10 in position.

As FIG. 5B illustrates, when the sealing member 14 of the laryngeal airway device 10 is seated, the distal end 34 of the pad 16 is lodged in the hypopharyngeal space 49 just above the esophagus 51. At the same time, the proximal end of the pad 16 presses against the epiglottis 42 forcing it in an anterior direction toward the tongue 43, thereby stretching the ary-epiglottic folds, which create a relatively firm rim at the laryngeal inlet. As shown in FIG. 5B, the pad 16 abuts and seals against the tensioned rim of the laryngeal inlet, with a part 56 of the anterior surface of the pad 16 projecting into the laryngeal vestibule 48.

As shown in FIG. 5B, a space is created on the anterior side of the airway device between the proximal anterior edge of the pad 16 and the air tube 12. This space can accommodate the extremely compliant tongue. FIG. 5B shows the tongue beginning to fall posteriorly into this space. When the tongue is accommodated in this space, it helps to seal the epiglottis 42 against the pad 16 and also helps to stabilize the airway device against accidental removal.

Figure 5C:
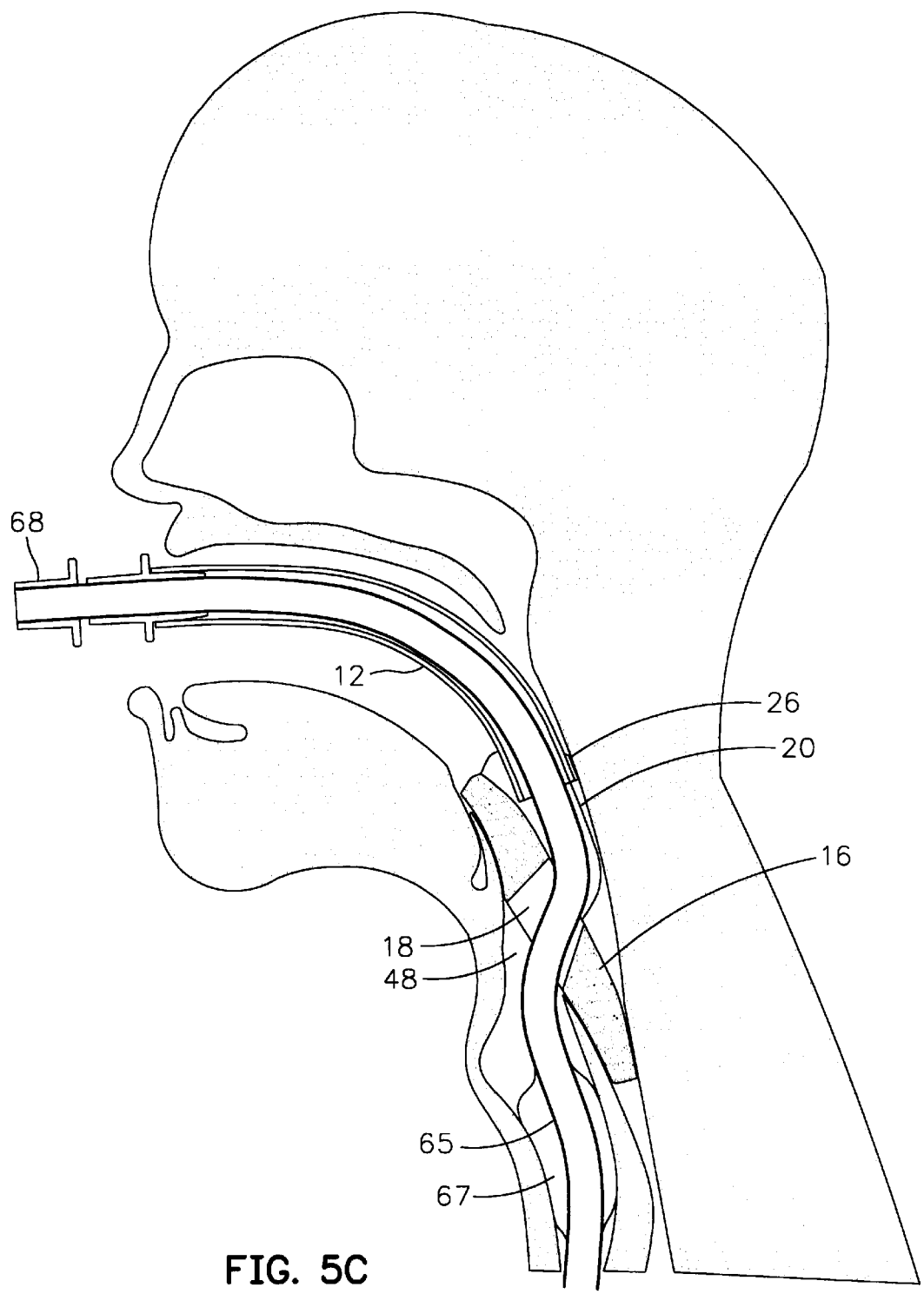
Figure 6:
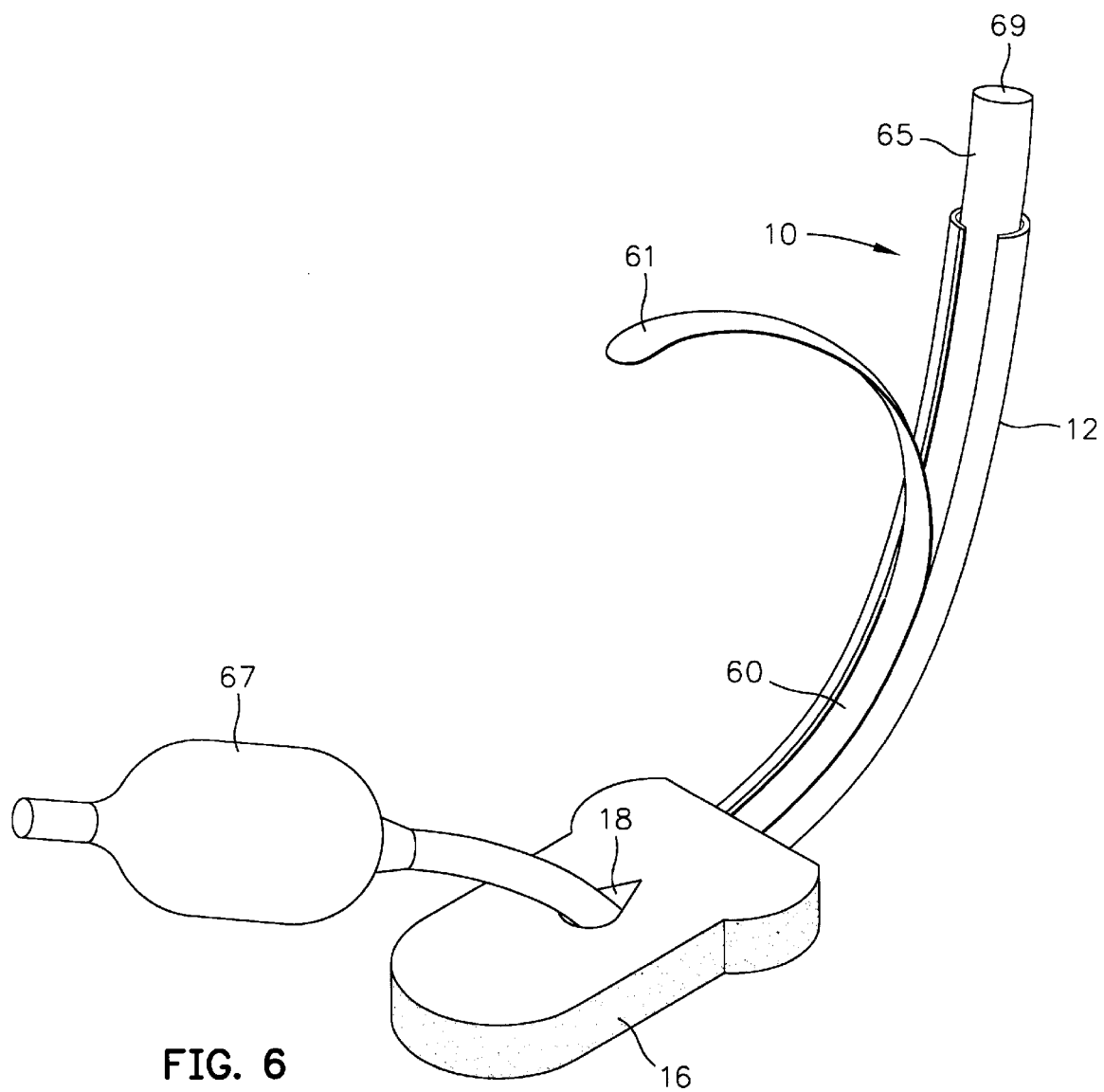
FIG. 6 shows an optional use of the first embodiment for intubation.

While we intend for our laryngeal airway device to be used as described for airway maintenance, we have nevertheless provided for the eventuality that intubation may be desired or indicated. This is shown in FIGS. 1A, 1B, 5C and 6. In such a case, a tear strip 60 is provided, for example, on the anterior side of the air tube 12 as shown in FIG. 6. The upper end of the tear strip 60 projects into a tab 61. The tear strip 60 is integral with the air tube 12. Preferably, to form the tear strip, the air tube 12 is extruded or molded with two partial thickness scored lines or grooves running along its entire length. Alternatively, the air tube 12 could be extruded with two small spaced-apart lumens within the wall of the tube 12. In either case, the air tube 12 is longitudinally weakened along the lines to create one or more seams along which the material of the air tube can be parted by tearing. The strip of tubing wall between the two grooves (or lumens) serves as the tear strip 60, which can be removed by grasping the tab 61 and pulling it away from the air tube 12. The tear strip 60 separates from the air tube 12 along the weakened grooves. Thus, when the tear strip 60 is removed, an open channel is created along the entire length of the air tube 12. Of course, the same result may be provided with a single seam. Further, the seams (or seam) may be located laterally or posteriorly on the air tube.

Should intubation be desired or indicated, an endotracheal tube, or fiber optic scope, can be passed through the laryngeal airway device and into the trachea by way of the air tube 12 and through the hole 18. This is shown in FIGS. 5C and 6, where an endotracheal tube 65 has been inserted through the air tube 12, distal end first. A distal balloon 67 on the endotracheal tube 65 is inflated, which seats the tube in the trachea. The strip 60 is then pulled away from the air tube 12, the endotracheal tube is rotated forwardly out of the slot created in the air tube 12 by the absence of the strip 60, and the laryngeal airway device 10 is pulled out of the patient's throat. In a quick maneuver, the laryngeal airway device 10 can be pulled over the proximal end 69 of the endotracheal tube. Alternatively, if the endotracheal tube 65 is connected to a ventilating apparatus, by a connector 68 for example, the laryngeal airway device 10 may be pulled out of the mouth along the endotracheal tube 65 to a point where, using scissors, the hole 18 may be enlarged and the support member 20 cut away so that the laryngeal airway device 10 can be pulled off of the endotracheal tube 65. Alternatively, the sealing member 14 can be constructed with a corresponding peel-away section, as explained later with respect to other embodiments.

Figure 7A:
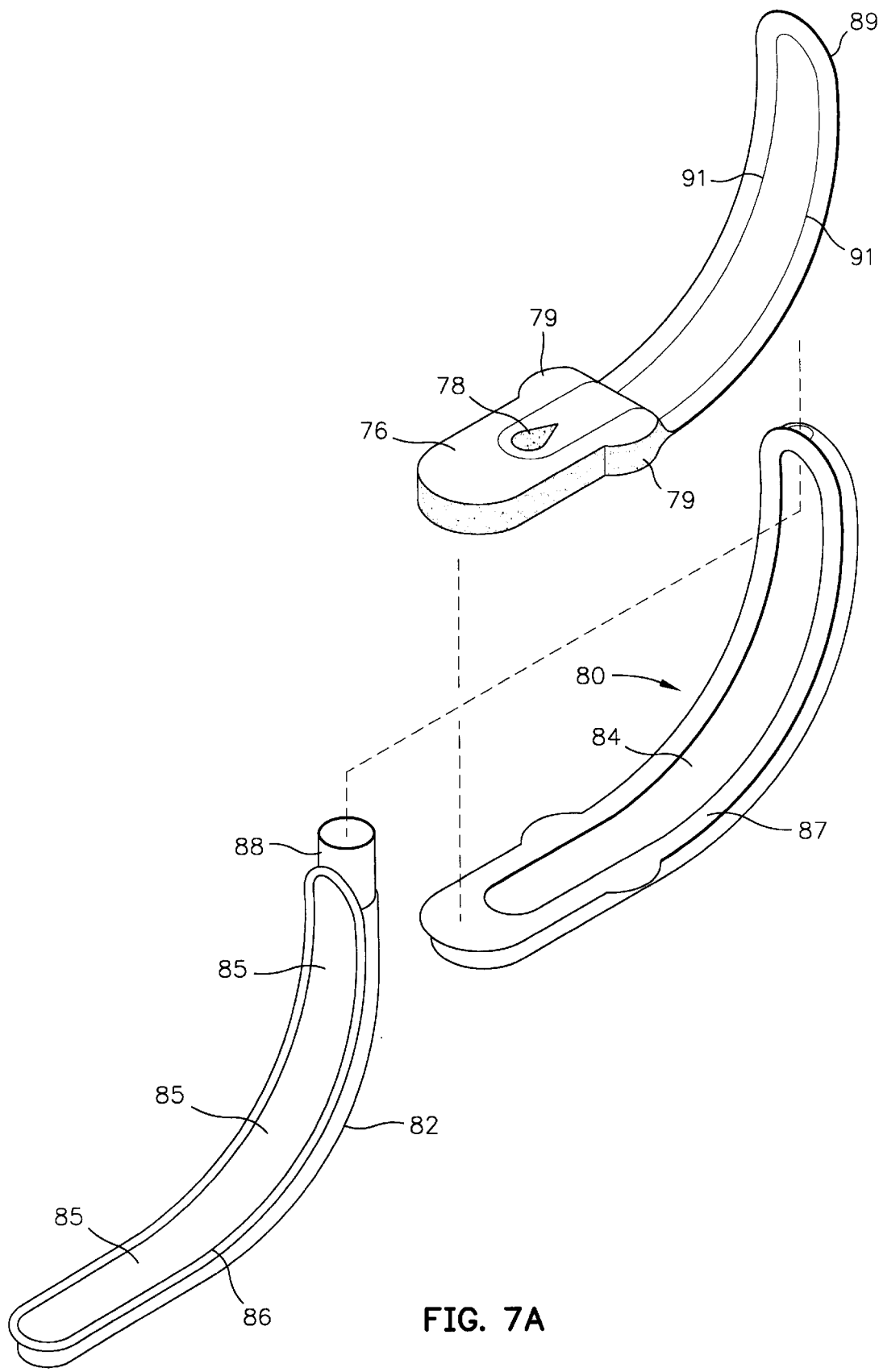
FIGS. 7A–7C show a second embodiment of the invention.
Figure 7B:
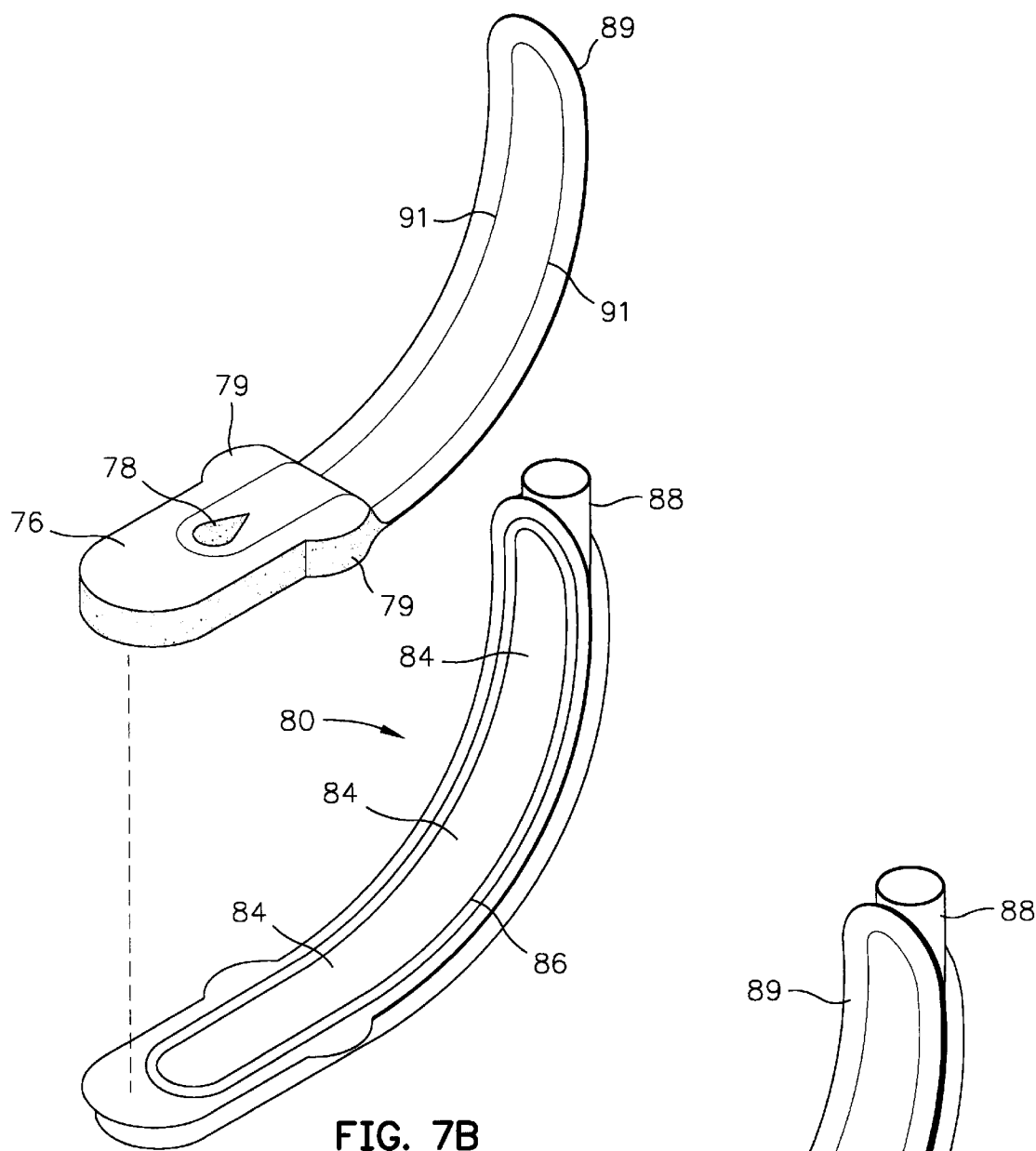
Figure 7C:
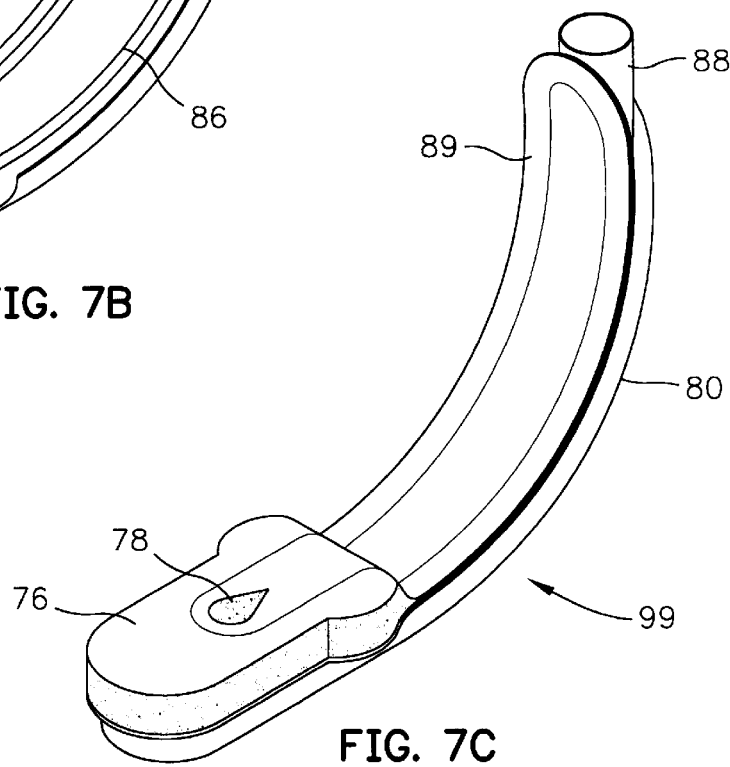

A second embodiment of the laryngeal airway device is illustrated in FIGS. 7A–7C. In FIG. 7A, the pad forming the anterior face of the laryngeal airway device is indicated by reference numeral 76. The pad 76 includes a teardrop-shaped hole 78. The pad 76 is bonded to a molded pad 80 forming the posterior surface of the laryngeal airway device. The molded pad 80 is preferably made of a foam plastic material selected to have flexibility and compressibility characteristics that provide structural support to the more compressible and conformable cushion portion of the laryngeal airway device. The molded pad 80 may also include a molded air channel 82 that is received in a trough 84. The molded air channel 82 is open at 85 and includes a peripheral lip 86 that is received on and bonded to the anterior surface 87 of the molded pad 80. A connector 88 is forward on the proximal end of the molded air channel 82. An additional strip of material 89 may be integral with the proximal end of the pad 76, attaching just above the wings 79. The strip of material 89 is preferably perforated at 91 to create a removable tear-strip along its length for intubation as described above with reference to FIGS. 5C and 6. Alternatively, the entire strip 89 of flexible material may be removable by parting an adhesive bond along its length. The strip 89 is glued or bonded to the peripheral lip 86 in order to confine airflow through the molded air channel 82, between the hole 78 and the connector 88. When assembled and bonded together, the pieces illustrated in FIGS. 7A and 7B form the single integral laryngeal airway device that is indicated by reference numeral 99 in FIG. 7C.

Figure 8A:
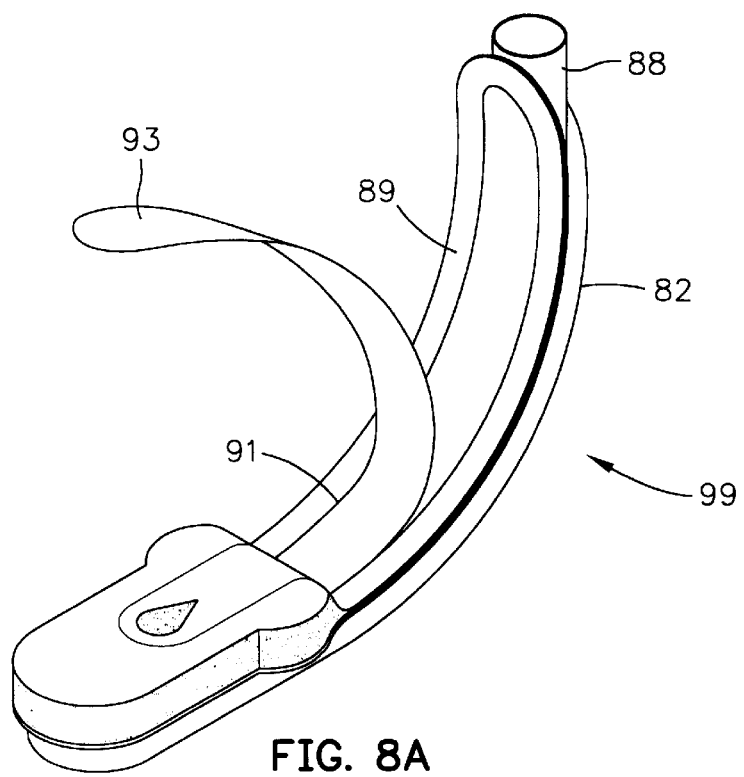
FIGS. 8A–8B illustrate the second embodiment optionally used for intubation.
Figure 8B:
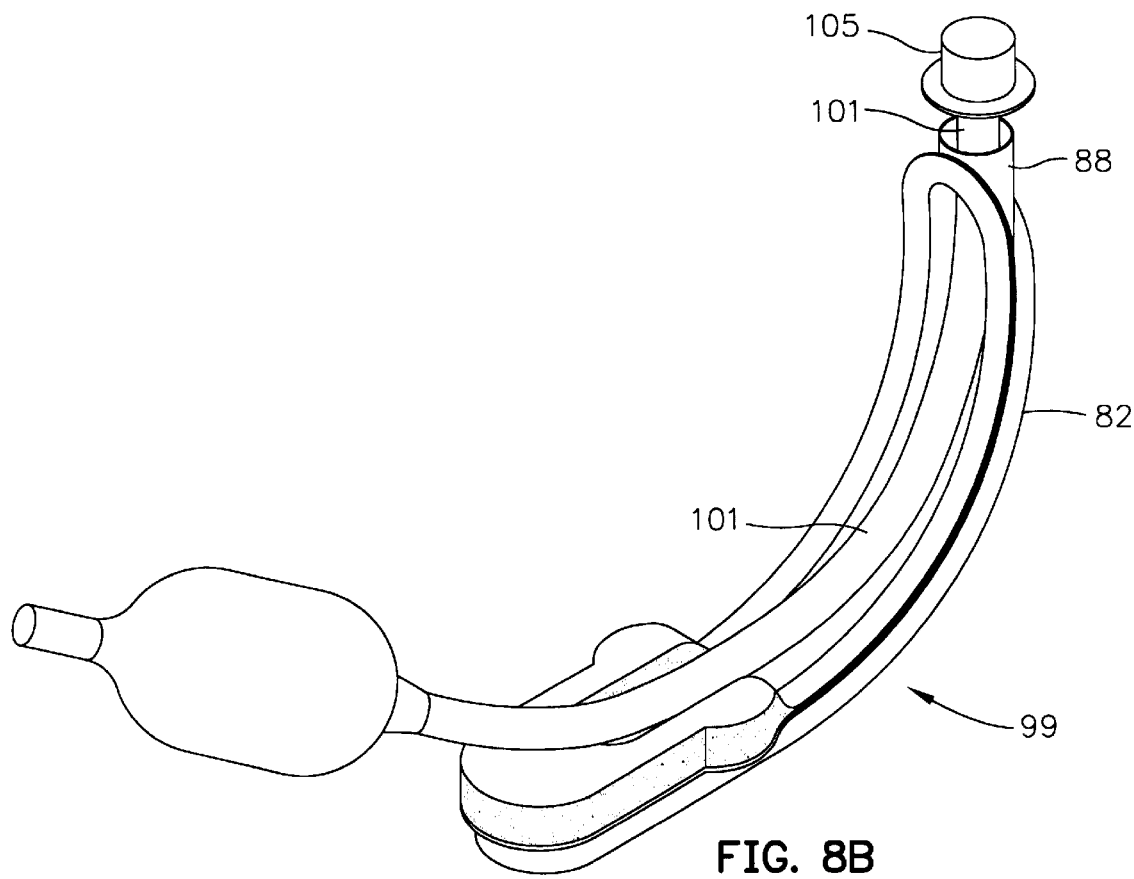

FIGS. 8A and 8B illustrate operation of the laryngeal airway device 99 when intubation is indicated or desired. In FIG. 8A, a strip 93 has been pulled away from the strip 89 along the perforations 91 so that the interior of the molded air channel 82 is exposed. FIG. 8B shows an endotracheal tube 101 inserted through the connector 88 of the molded air channel 82. With a fitting 105 already attached to the proximal end of the endotracheal tube 101, the laryngeal airway device 99 can be removed from the endotracheal tube 101 by cutting away the structure of the device 99 around the socket 88. Alternatively, before the fitting 105 is placed on the endotracheal tube 101, the entire laryngeal airway device 99 can be pulled over the distal end of the endotracheal tube 101 in a quick maneuver.

Figure 9A:
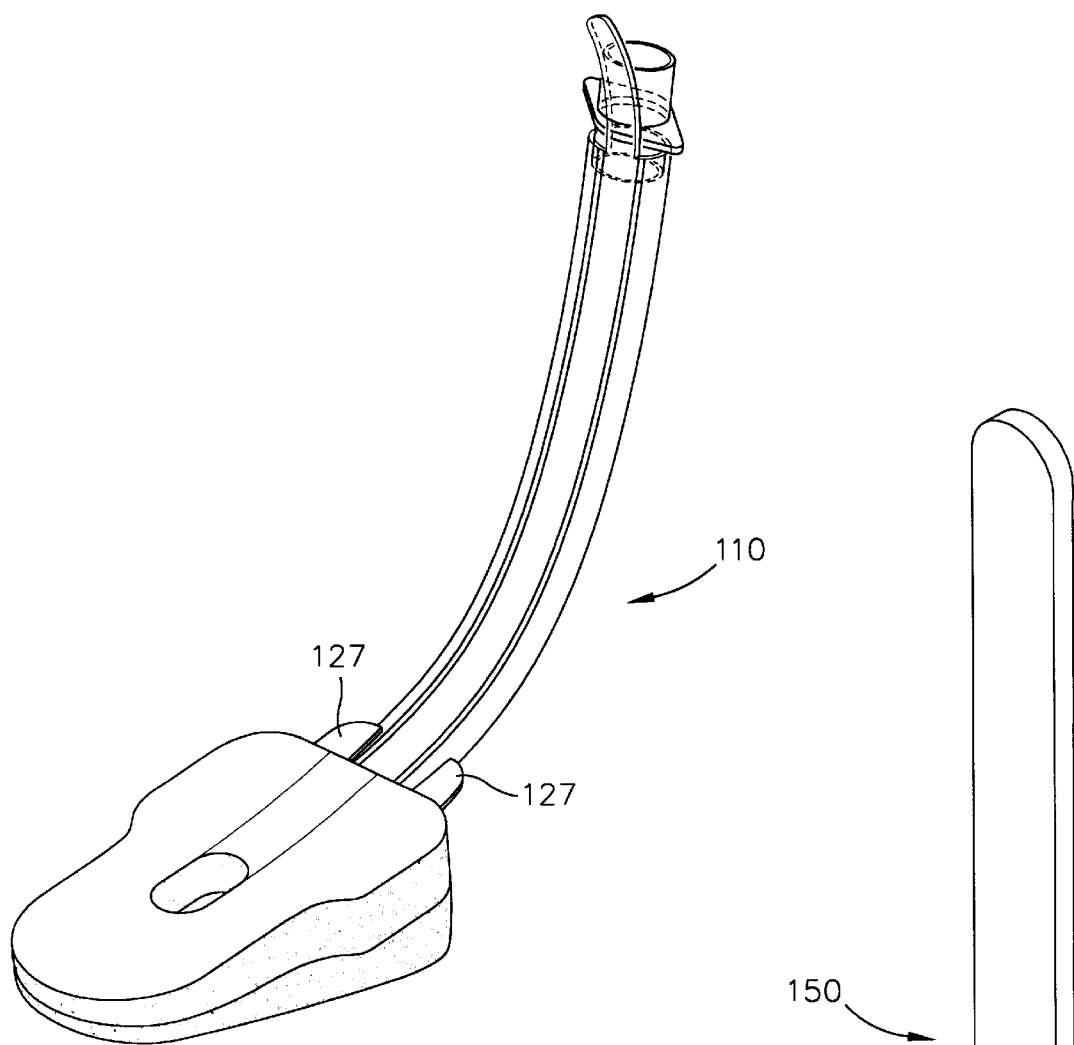
FIGS. 9A–9C illustrate a third embodiment with an optional means for retaining an optional pharyngeal blade to the laryngeal airway device.
Figure 9C:
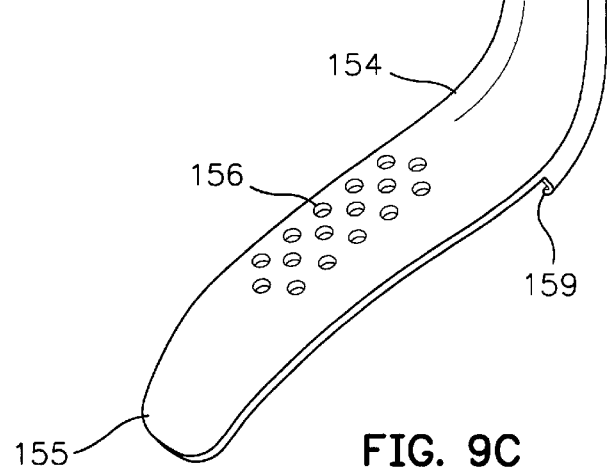
Figure 9B:
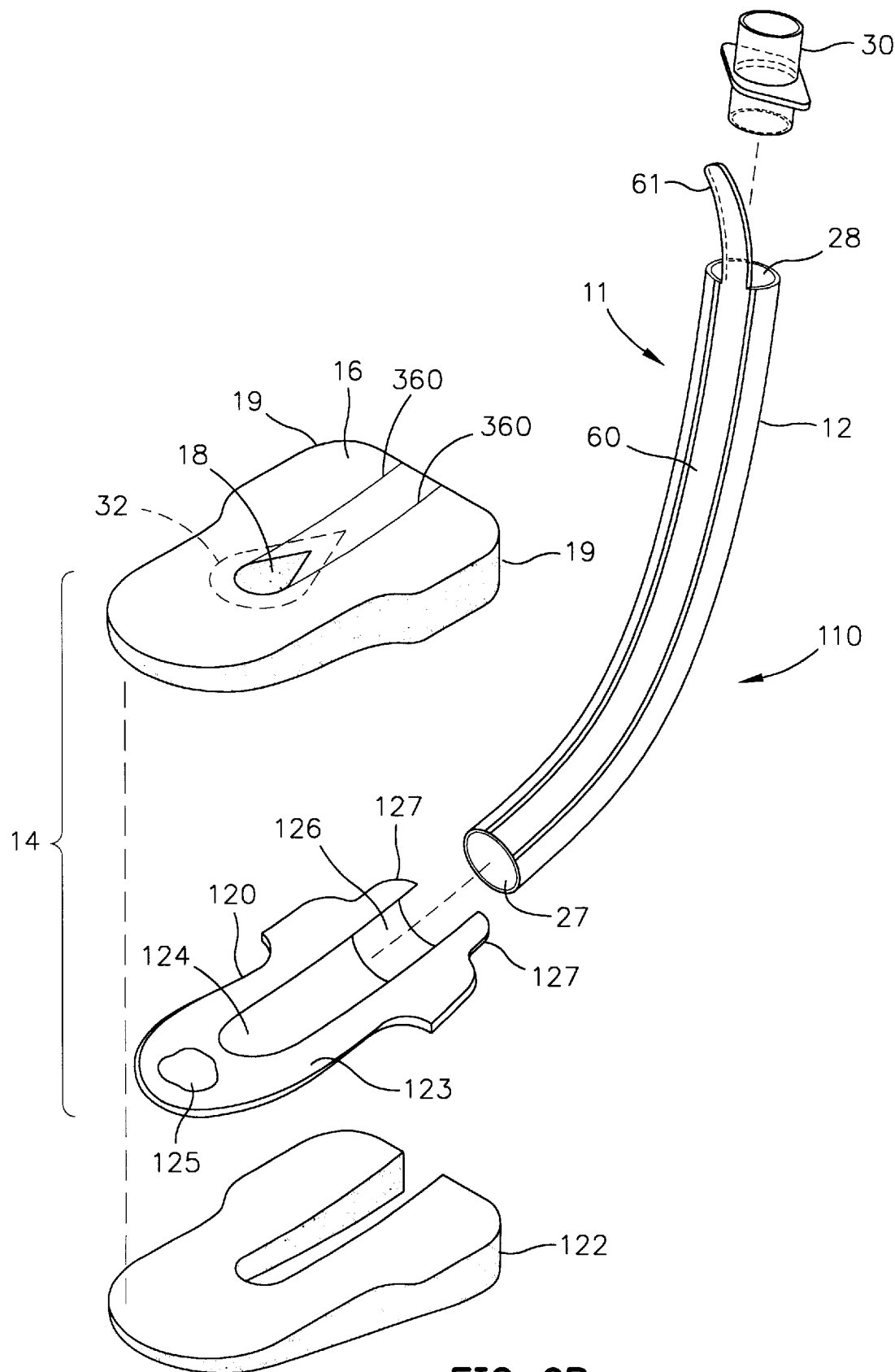
Figure 10A:
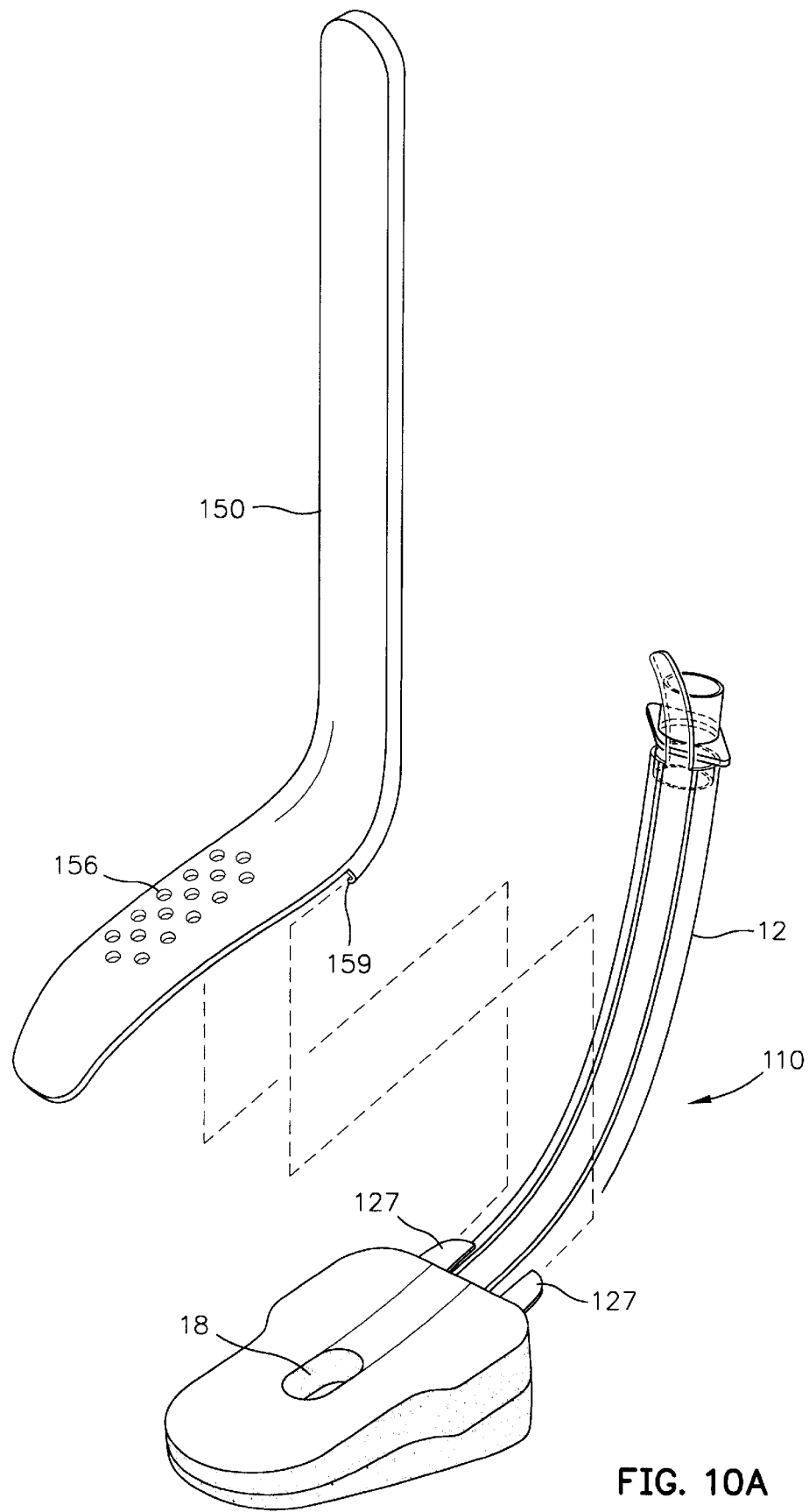
FIGS. 10A and 10B illustrate attachment of the pharyngeal blade on the optional retaining means of the laryngeal airway device.
Figure 11:
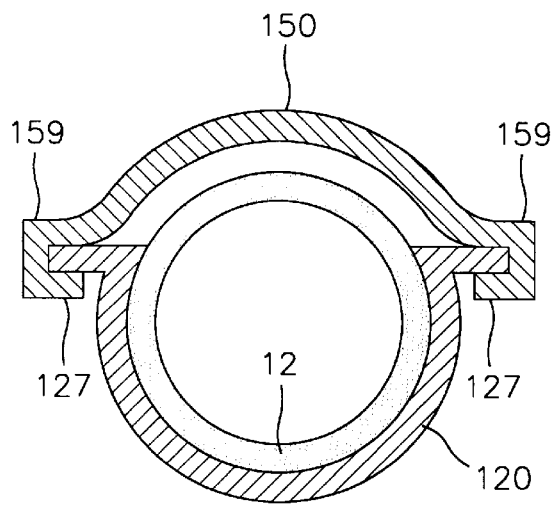
FIG. 11 illustrates, in a cross sectional view, how the optional retaining means functions to retain the pharyngeal blade on the laryngeal airway device.
Figure 10B:
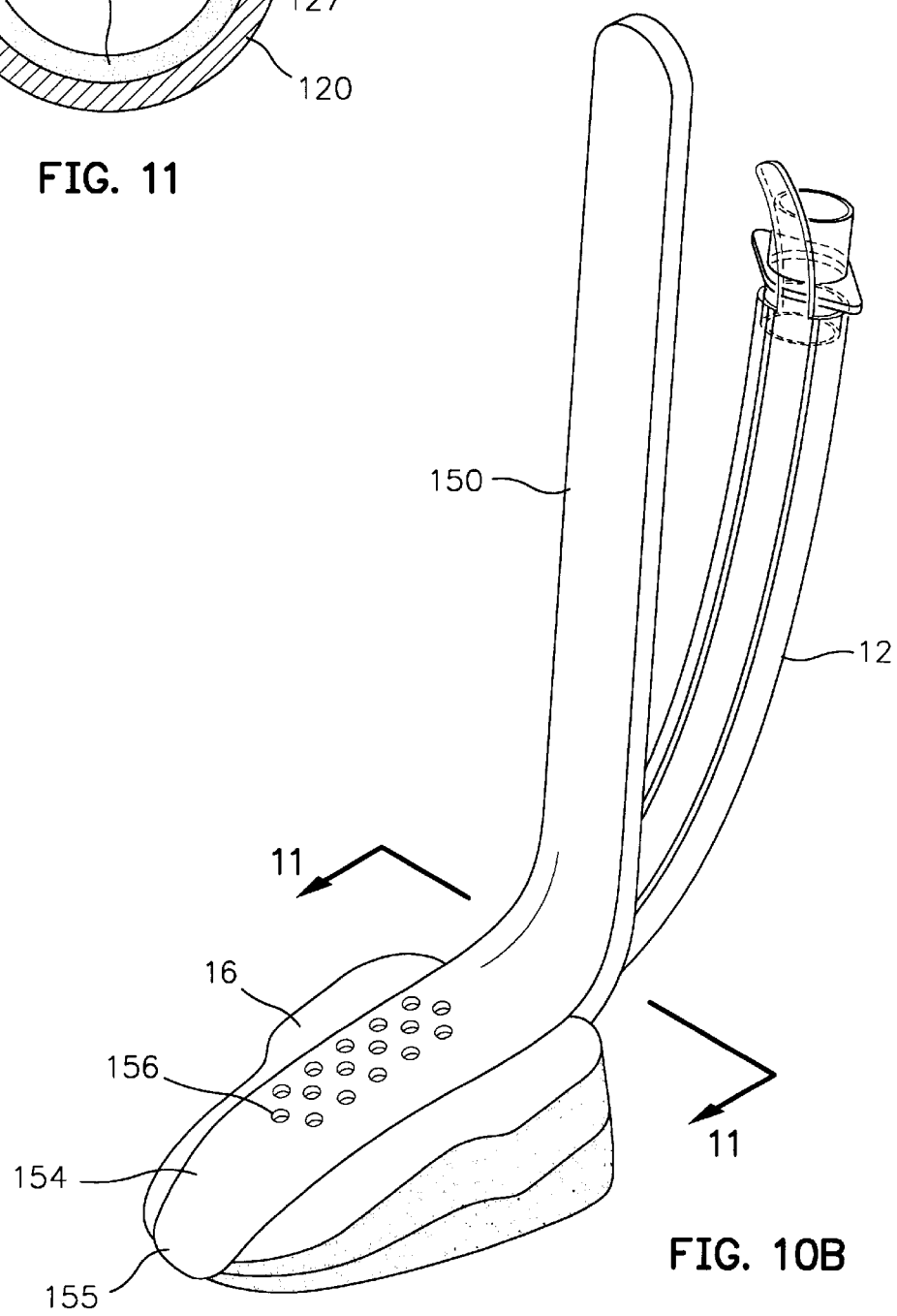

FIGS. 9A–9C illustrate a third embodiment of the laryngeal airway device that includes a molded plastic support member 120 having an open slot or passageway 124 and a partial socket at its rearward end 126 to accept the distal end 27 of the air tube 12. A laryngeal airway device 110 is assembled by suitably bonding the air tube 12, pad 16 and support member 120 together. For example, with the distal end 27 of the air tube 12 glued into the socket 126 of the slot 124, the under surface of the pad 16 can be glued to the opposing surface 123 of the support member 120. A posterior pad 122 made of a foam material or an inflatable bladder may be mounted to the posterior side of the support member 120. The posterior pad 122 optimally serves as a cushion against the posterior wall of the pharynx, elevates the device anteriorly toward the laryngeal inlet, and helps to stabilize the device, preventing it from shifting position during use. Optionally, a gauze or cloth layer may be added to the posterior pad 122 to frictionally engage the posterior wall of the pharynx, for further stability. If the posterior pad 122 is used, the molded plastic support member 120 is sandwiched internally between the pad 16 and the posterior pad 122. The support member 120 is preferably made of a molded flexible plastic that is stiffer than the materials of which the pad 16 and the optional posterior pad 122 are made. The support member 120 serves to anchor the distal end 27 of the air tube 12. Preferably the socket 126 of the support member is an incomplete ring with a void in its anterior wall. The void corresponds with the removable strip portion 60 of the air tube 12 (described above). Preferably, the support member 120 has an elbow portion immediately distal to the distal end 27 of the air tube 12, which redirects air, and or a fiber optic scope or endotracheal tube through the hole 18 in the pad 16, and toward the laryngeal inlet. Optionally, the support member 120 may include a midline depression 125 in the plane of its anterior surface 123, distal to the elbow. This depression may be designed to accommodate the rigid ringlike cricoid cartilage, by allowing the cricoid cartilage and the cushion supporting it to be depressed through the plane of the surface 123. Preferably, the support member 120 also includes retaining flanges 127. These are intended to retain a pharyngeal blade 150 having retaining slots, one of which is indicated by 159. The retaining slots 159 are set back from the distal end 155 of the lower leg 154 of the pharyngeal blade 150. As FIGS. 10A and 10B illustrate, the pharyngeal blade 150 is attached to the laryngeal airway device 110 by the interlocking action between the retaining flanges 127 on the support piece 120 and the retaining slots 159 on the blade 150. When thus retained, the lower leg 154 compresses the pad 16, with the distal end 155 of the blade extending slightly beyond the distal end of the pad 16. FIG. 11 shows, in a cross section taken along 11—11 in FIG. 10B, the retention of the laryngeal blade 150 by engagement of the elongate slots 159 with the flanges 127 on the support member 120. The holes 156 align with the hole 18 to permit ventilation through the laryngeal inlet, by way of the air channel 12.

An alternate means of engagement between the blade 150 and the laryngeal airway device 110 is illustrated in FIGS. 12A and 12B. FIG. 12B is a cross section taken at 12B—12B in FIG. 12A, with the blade 150 attached to the laryngeal airway device 110. In this case, each of the flanges 127 includes a respective hole 128. Further, in the blade 150, the blade portion 154 includes, set back from the distal tip 155, a pair of projections 162 on the posterior side of the blade 150, each of which extends toward the distal end 155 and which may be received in a respective one of the holes 128 to attach the blade 150 to the laryngeal airway device 110.

Figure 13A:
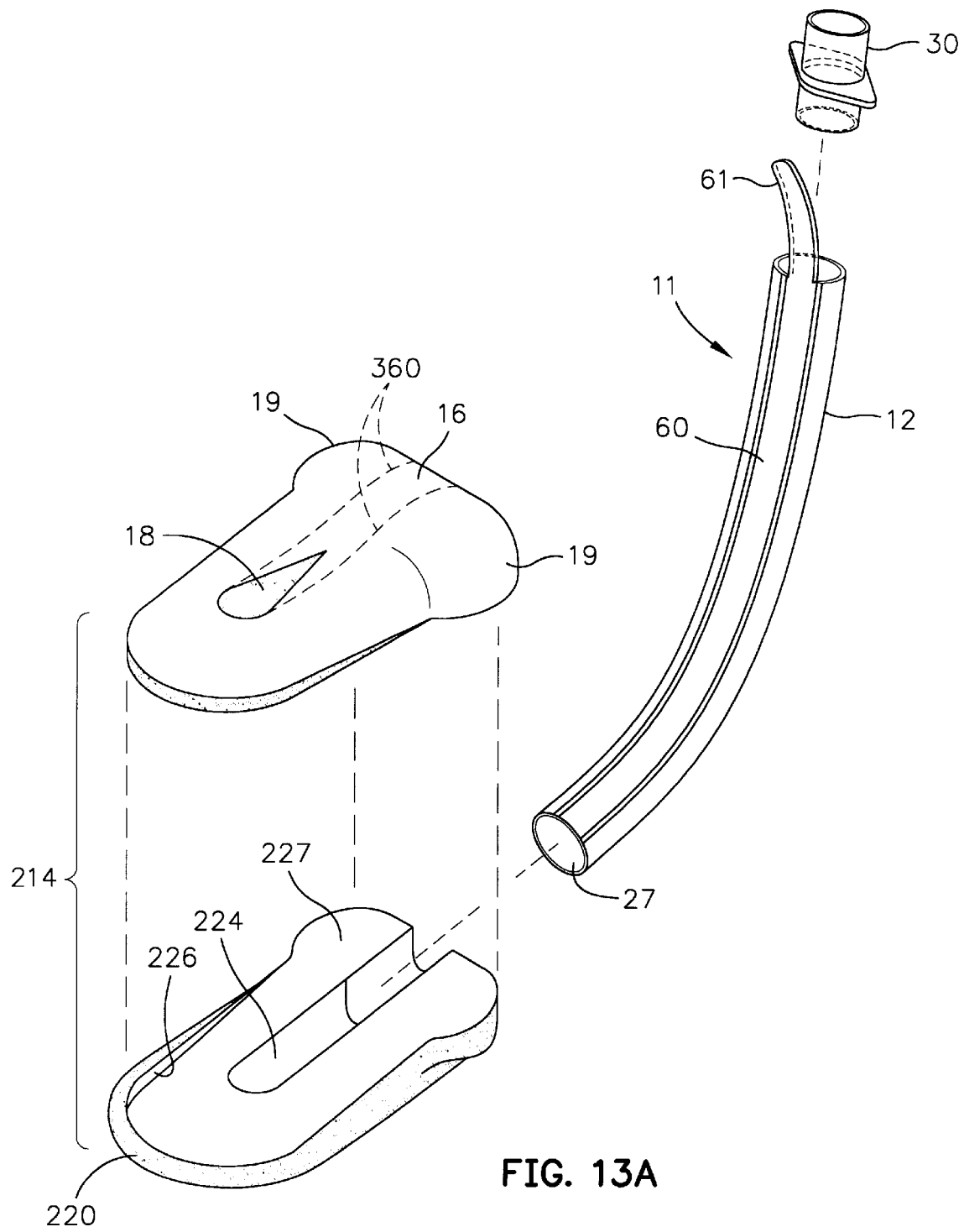
FIGS. 13A and 13B illustrate a further alternate embodiment of the invention.
Figure 13B:
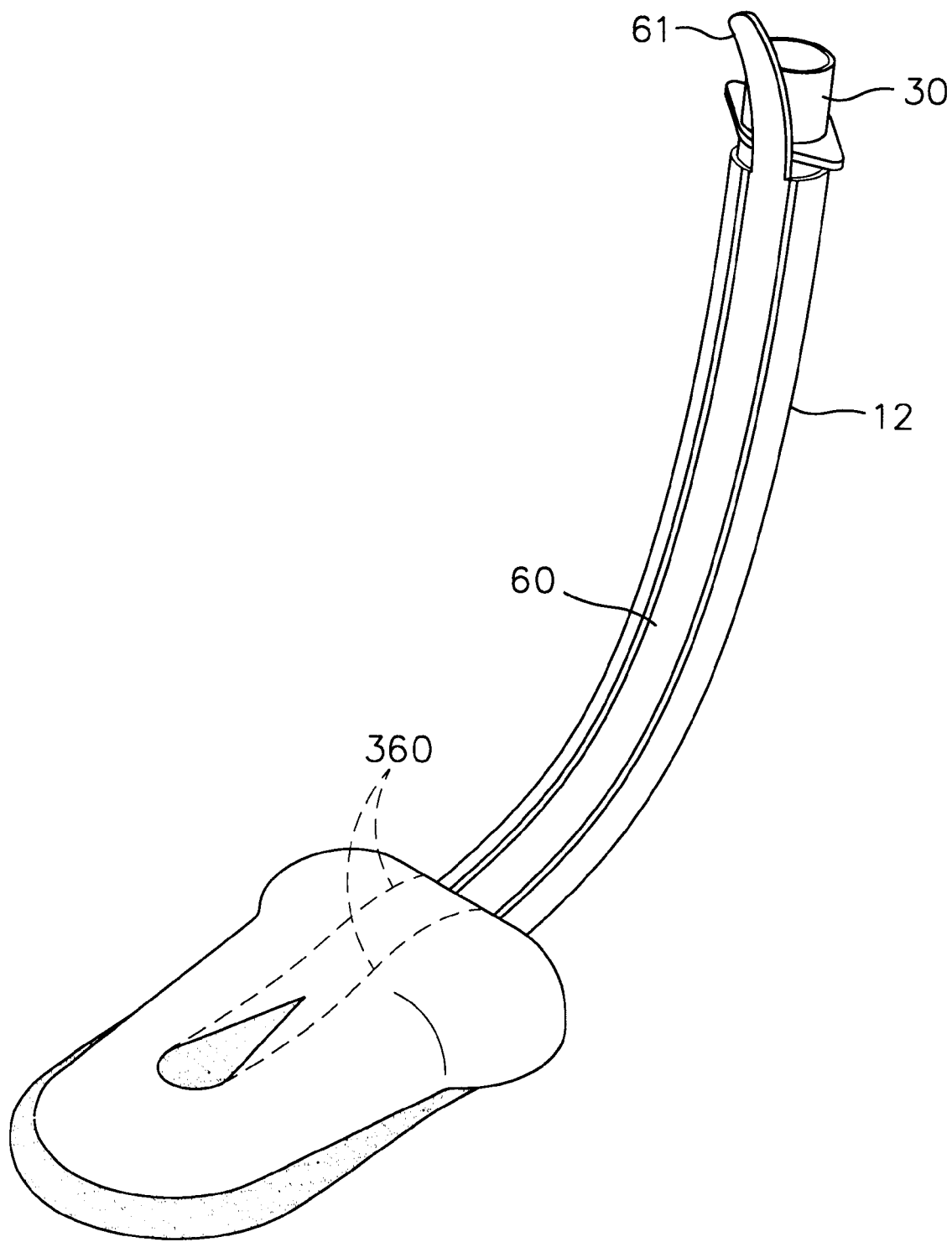

Refer now to FIGS. 13A and 13B which show a fourth embodiment of the invention. In this embodiment, the air channel 11 and pad 16 of soft, compliant material are as described in connection with the first embodiment illustrated in FIGS. 1A, 1B and 1C. In this embodiment, however, a sealing member 214 comprises a support member in the form of a pad of compliant material 220 that is stiffer and less compliant than the material of which the pad 16 is made. This pad is termed the "posterior pad", while the pad 16 may be termed the "anterior pad". The posterior pad 220 includes a passageway 224 and a shaped recess 226 having an anterior surface 227. With the distal end 27 of the air tube 12 received in the passageway 224, the anterior pad 16 is bonded, for example, by gluing, to the surface 227 of the posterior pad 220. This forms the passageway 224 into an air passageway that communicates between the distal end 27 and the hole 18. As thus constructed, the alternate embodiment illustrated in FIGS. 13A and 13B operates as described above for airway management, and may have any of the optional adaptations for insertion and for intubation that are disclosed in connection with previously-described embodiments.

Finally, for ease of ETT placement, FIGS. 9B, 13A and 13B shows lines of weakness 360 in the pad 16 that extend from the wide portion of the teardrop-shaped hole 18 to the proximal edge of the pad 16. These lines represent a tear strip that is generally aligned with the tear strip 60 and that can be removed with the tear strip 60 to completely open the laryngeal airway device to facilitate removal of the laryngeal airway device from an endotracheal tube, without requiring scissors to assist in removal.

The fifth embodiment of our invention forms an effective fluid seal with a laryngeal inlet, positions the laryngeal airway device very accurately and dependably with respect to the laryngeal inlet, and improves the ease of insertion of the laryngeal airway device into a patient.

It should be noted that, even when the epiglottis is tensioned by an anterior rotation (that is, one toward the front of the neck), the lateral ary-epiglottic folds of certain patients have a pronounced concave scallop in the lateral rims of the larynx. In some patients, extreme scalloping poses a significant challenge to the engagement of the anterior surface of the laryngeal airway device with the edge of the larynx. Manifestly this can affect the quality of the seal that our device makes with the laryngeal inlet.

The fifth embodiment of our laryngeal airway device provides an increased angle of the anterior surface on the sealing member lateral to the hole through the sealing member. The increased angle anticipates and accommodates a pronounced scallop in the lateral rim of the laryngeal inlet, increasing the reliability of a seal formed therewith by the sealing member of the device.

The fifth embodiment also increases the accuracy which with our device can be placed in the throat of a patient, and enhances the dependability of the seal with the upper portion of the laryngeal inlet.

Figure 14:
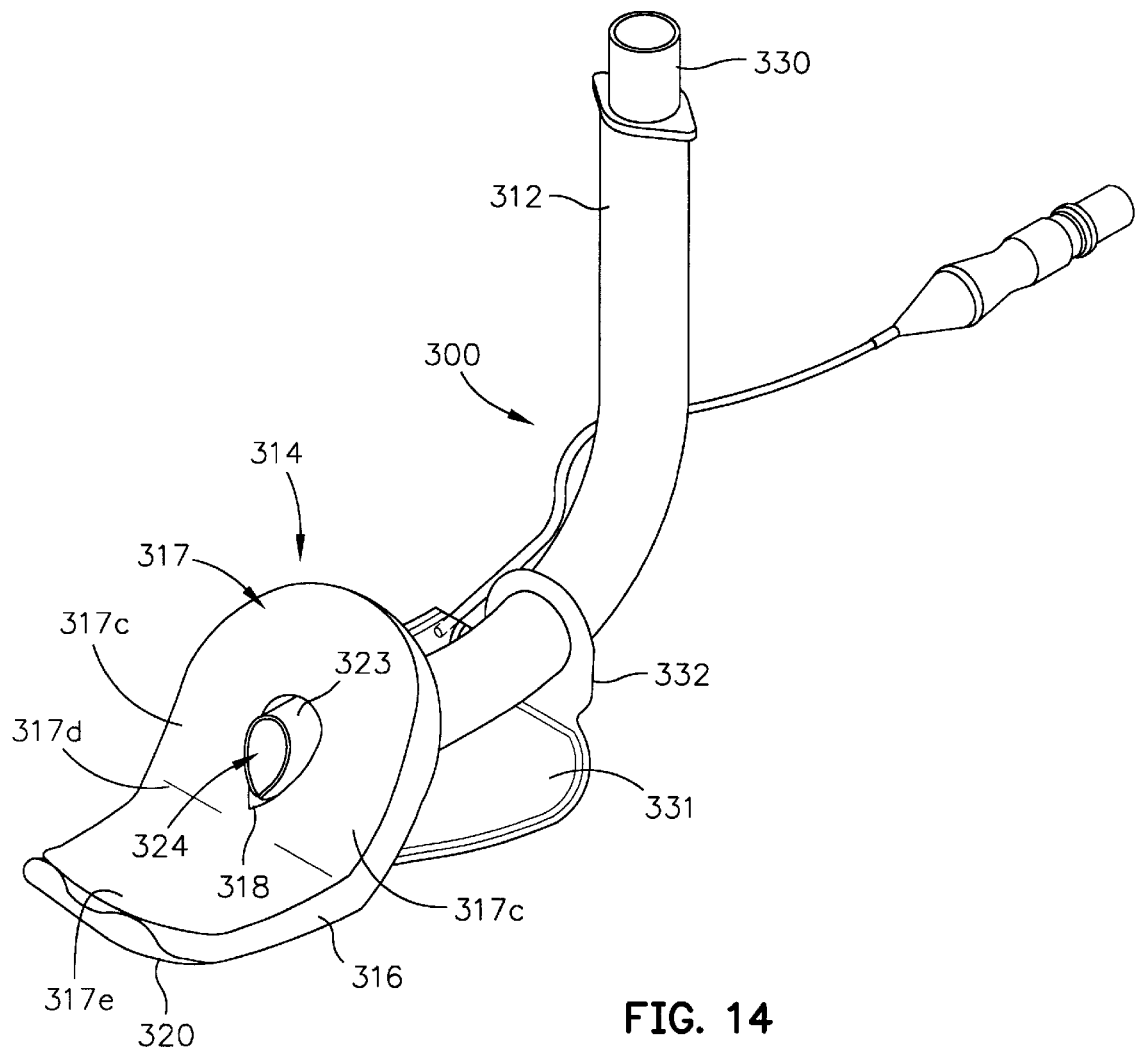
FIG. 14 is an isometric view of a fifth embodiment of the invention.
Figure 15:
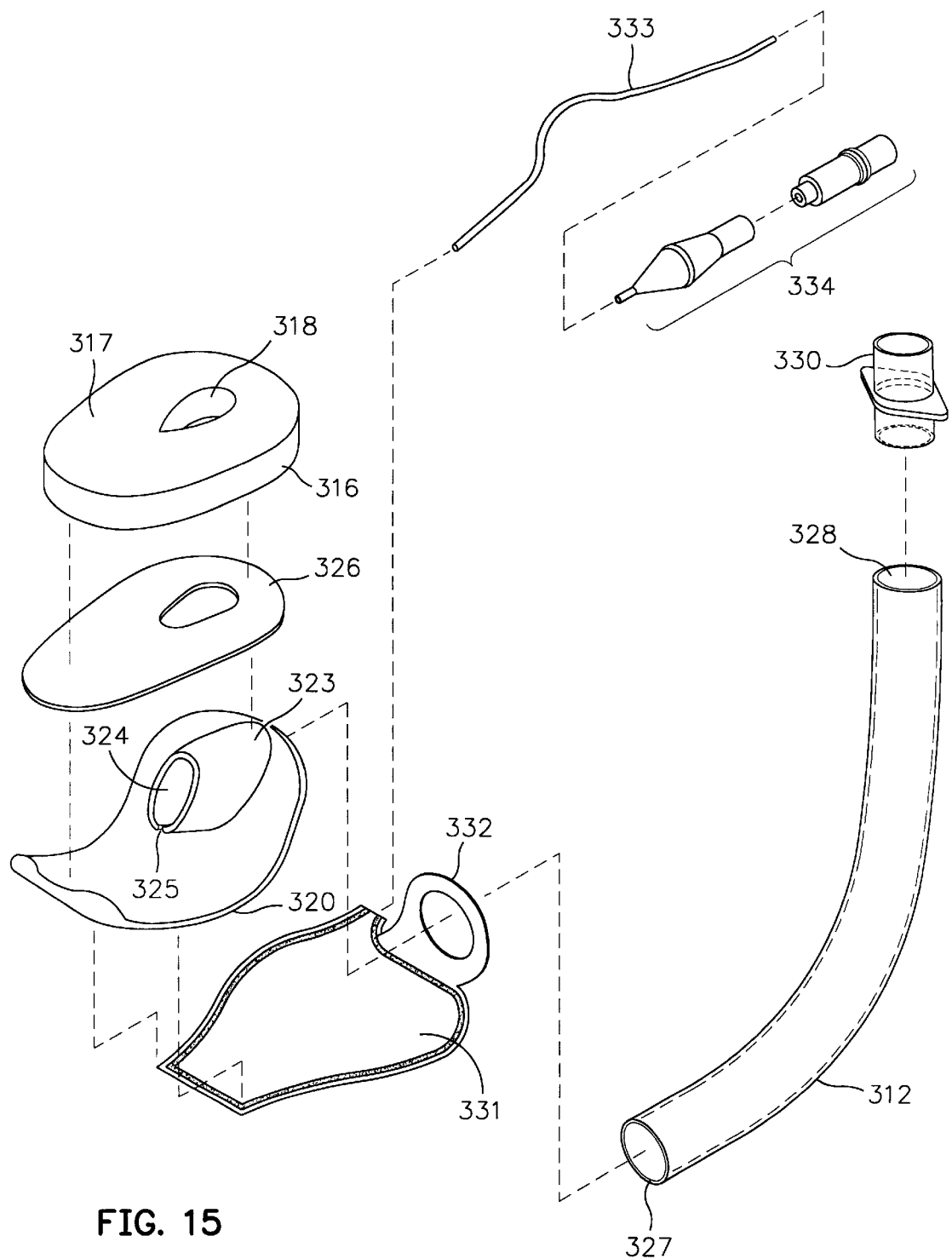
FIG. 15 is an exploded assembly view of the fifth embodiment.
Figure 16:
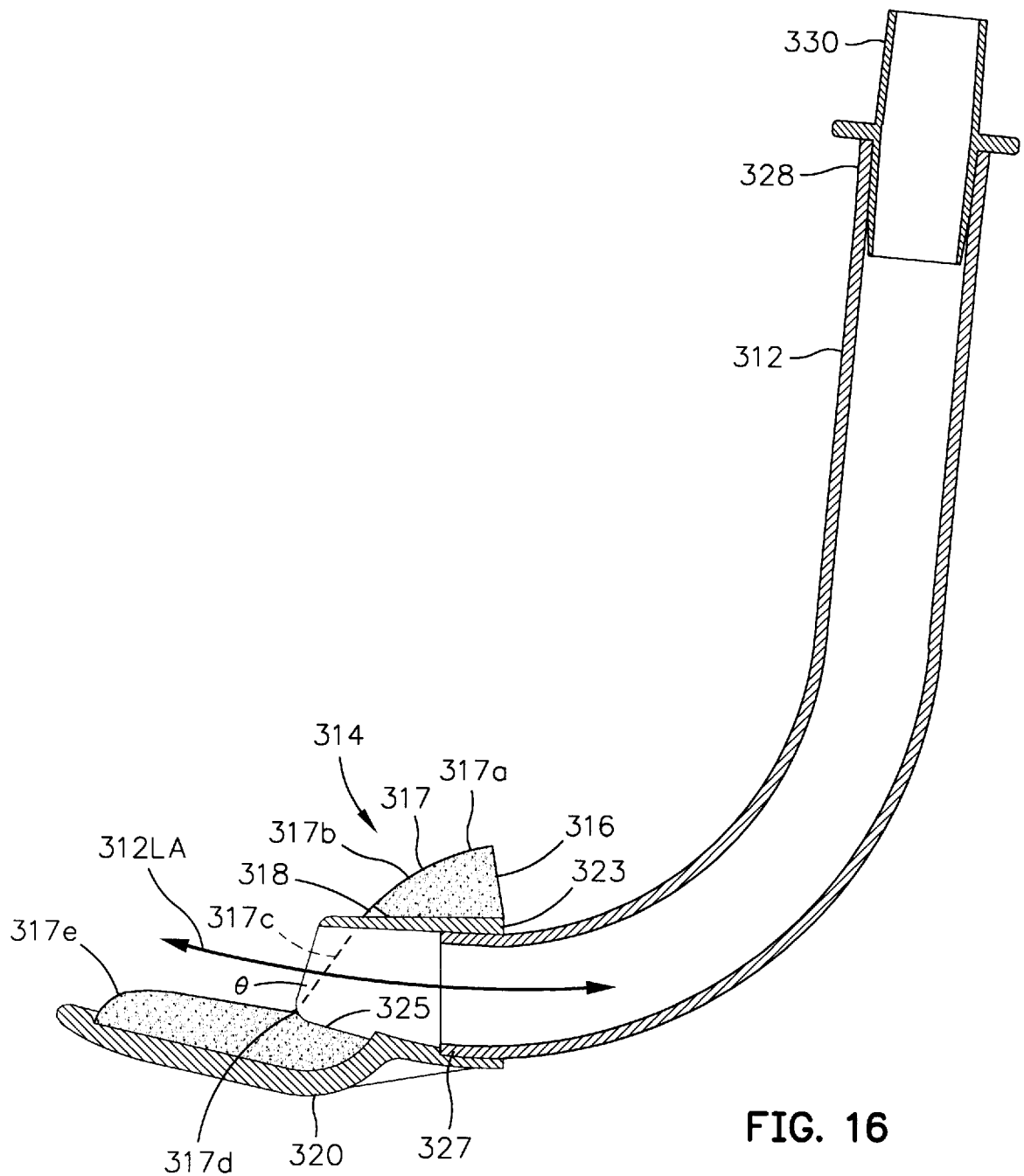
FIG. 16 is a side sectional view of the fifth embodiment.
Figure 17:
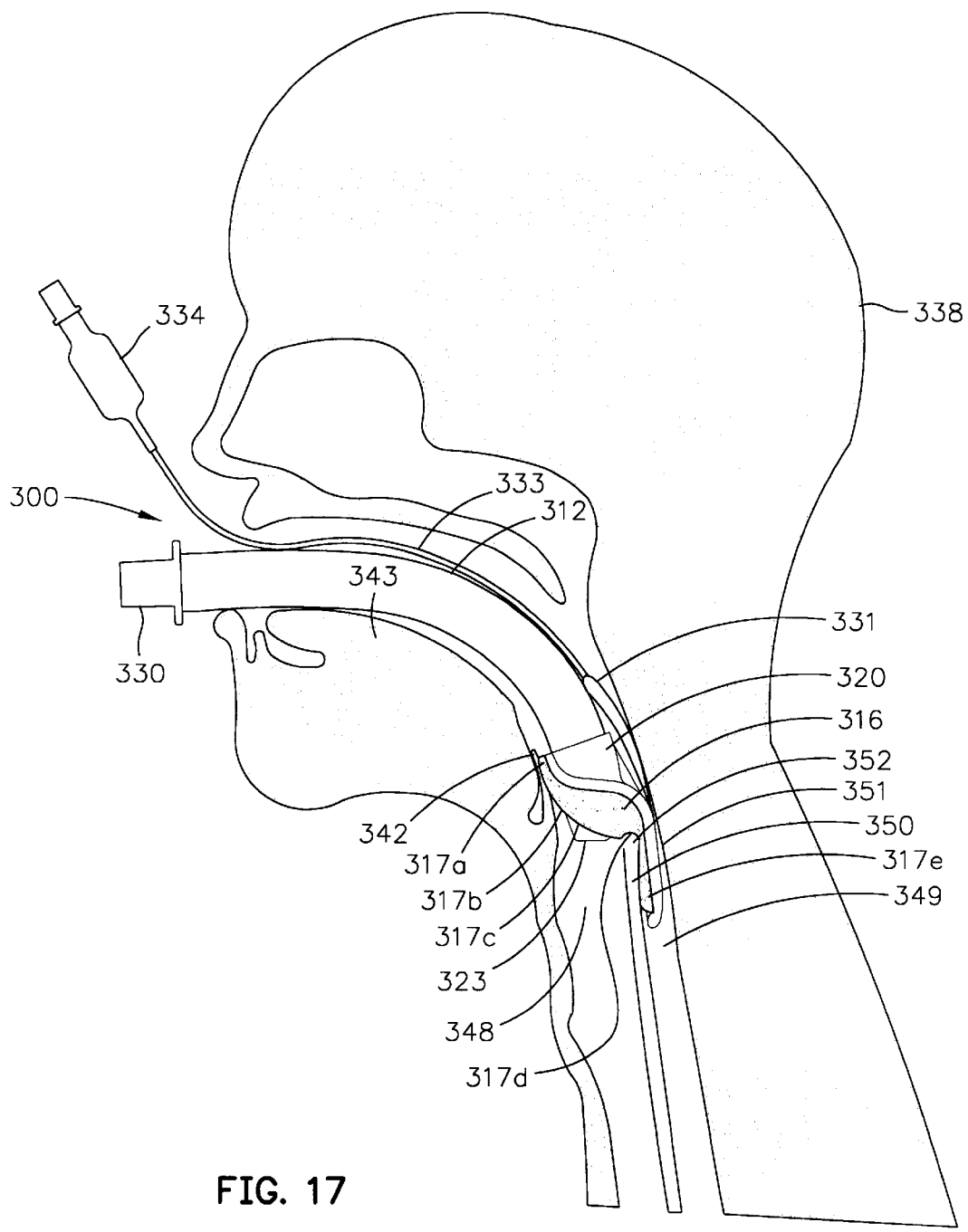
FIGS. 17 and 18 are schematic illustrations of the fifth embodiment in use, sealing the laryngeal inlet.

The fifth embodiment of our laryngeal airway device is illustrated in FIGS. 14, 15, 16 and 17. FIG. 14 is an isometric view of the fifth embodiment, assembled. FIG. 15 is an isometric exploded view showing the elements of the fifth embodiment, FIG. 16 is a side sectional view of the fifth embodiment. FIG. 17 is a side elevational view of the fifth embodiment after having been advanced against the laryngeal inlet. Refer now to all of these figures for an understanding of the structure and parts of the fifth embodiment of our laryngeal airway device, which is indicated generally by reference numeral 300. The device 300 includes an air tube 312 and a sealing member 314. The sealing member 314 includes a pad 316 with an anterior surface 317. The tube 312 and pad 316 may be formed with the materials described above in respect of embodiments one through four. A hole 318 opens through the anterior surface 317 and the pad 316. As with the above-described embodiments, the hole 318 is substantially in the midline of the pad 316. It may be teardrop-shaped, narrowest in its transverse dimension, which is smaller than the transverse dimension of the laryngeal opening with which it is adapted to seal. The sealing member 314 further includes a sigmoid-shaped, molded plastic support member 320 having a sleeve 323 that defines a passageway 324. The distal end 327 of the air tube 312 is received in the rear opening of the sleeve 323. When assembled, the air tube 312 communicates through its distal end 327, the sleeve 323, and the hole 318.

The sleeve 323 preferably has the longitudinal shape of a truncated cone that funnels the larger diameter distal end 327 of the air tube 312 down to the smaller diameter of the hole 318. Alternately, the shape of the sleeve 323 could be tubular. The sleeve 323 is preferably tear-drop shaped in cross-section, with the point of the tear-drop at 325 oriented posteriorly (toward the bottom) with respect to the sealing member 314. The teardrop shapes of the hole 318 and sleeve 323 approximate the shape of the supraglottic larynx, with the point of the sleeve 323 fitting between the arytenoid cartilages. Alternatively, these shapes could be substantially oval or round in cross-section. At the apex of the teardrop shape of the sleeve 323, at least one longitudinal cleft is provided, extending from the distal margin of the sleeve 323 toward the distal end 327 of the air tube 312. This cleft weakens the wall of the sleeve 323, reducing the risk of injury to the larynx. Preferably the cleft 325 is on the posterior wall at the apex 325 of the sleeve's teardrop shape. Therefore, the wall of the collar, when contacting the arytenoid cartilages, is very flexible and the contact is non-traumatic. Preferably the anterior portion of the wall of the sleeve 323 is intact and therefore stiffer than the posterior portion, thereby enabling the sleeve 323 to support the epiglottis on its anterior wall portion. Finally, the cleft at 325 allows expansion of the sleeve 323, particularly at its distal margin, to accommodate the passage of an oversized tracheal tube through its lumen.

A connector 330 is mounted to the proximal end 328 of the air tube 312. An inflatable balloon 331 is mounted to the tube 312 by attachment to the posterior surface of the support member and by a collar 332 that slides over the outer surface of the air tube 312 near its distal end 327. The balloon 331 is thereby retained on the air tube 312, posteriorly to the sealing member 314.

The fifth embodiment as so far described is assembled by suitably bonding the pad 316 to the support member 320 by way of, for example, an adhesive layer 326, and then bonding the distal tip 327 of the air tube 312 in the posterior opening of the sleeve 323. Thus assembled, an air passageway opens from the proximal end 328 of the air tube 312 through the tube 312 and the sleeve 323, and extends through the hole 318. With connection of a ventilating device to the connector 330, controlled, artificial respiration can be provided when the fifth embodiment 300 is seated in the throat of a person, as will be described further.

As shown in FIGS. 16 and 17, the anterior surface 317 of the pad 316 has a proximal anterior extension 317a that transitions into a convex curve 317b. The convex curve 317b of the anterior surface transitions, on either side of the hole 318, into lateral anterior surface portions 317c. From the bottoms of the lateral anterior surface portions 317c, the anterior surface 317 transitions through a concave curve 317d to a distal extension 317e. As can be best appreciated from FIGS. 16 and 17, the distal extension 317e, the concave curve 317d, the lateral anterior surface portions 317c, the convex curve 317b, and the proximal anterior extension 317a of the anterior surface 317 combine to give the anterior surface a substantially sigmoid shape. The convex curve 317b in the anterior surface 317, together with the lateral anterior surface portions 317c, oppose the concave scallop frequently occurring in the lateral rim of the laryngeal inlet, thereby creating an improved fluid seal with the inlet's rim.

The angle θ which the lateral anterior surface portions 317d forms with an extension of a longitudinal axis 312LA of the distal end 327 of the air tube 312 is preferably approximately 55°. Alternatively, this angle may be in the range of approximately 30° to approximately 90°.

The difficulty of dependably engaging the laryngeal inlet by an instrument without visualization is well recognized in the medical arts. For the laryngeal airway device of our invention to operate dependably, the ventilation hole 318 (and the distal end of the sleeve 323) must accurately oppose the orifice of the laryngeal inlet. It is preferable that the accurate alignment of the ventilation hole in our device with the laryngeal inlet be accomplished during "blind" or non-visualized insertion. The design of our fifth embodiment accurately and dependably positions the laryngeal airway device with respect to the laryngeal inlet, as now described.

Figure 18:
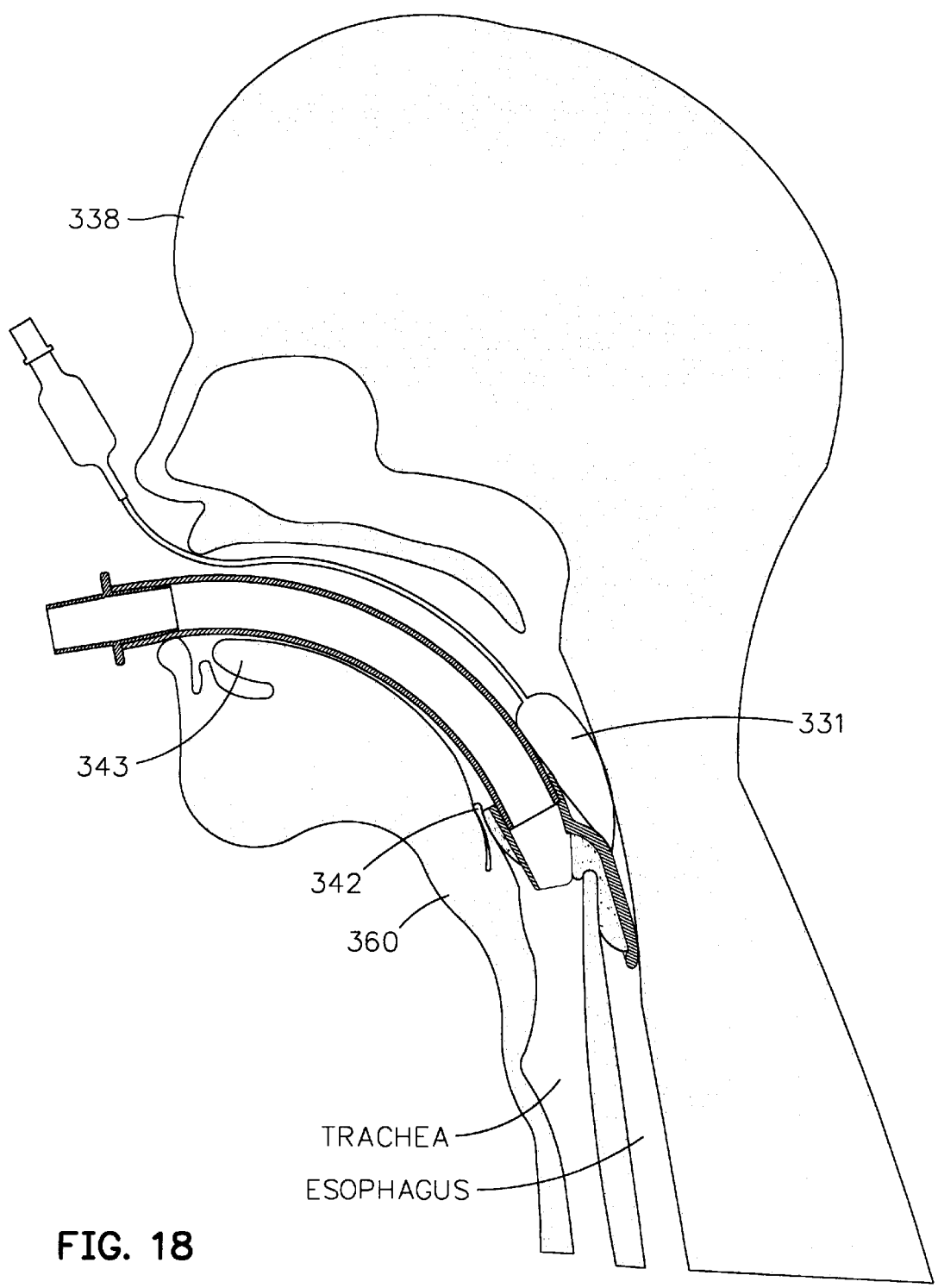
Figure 19:
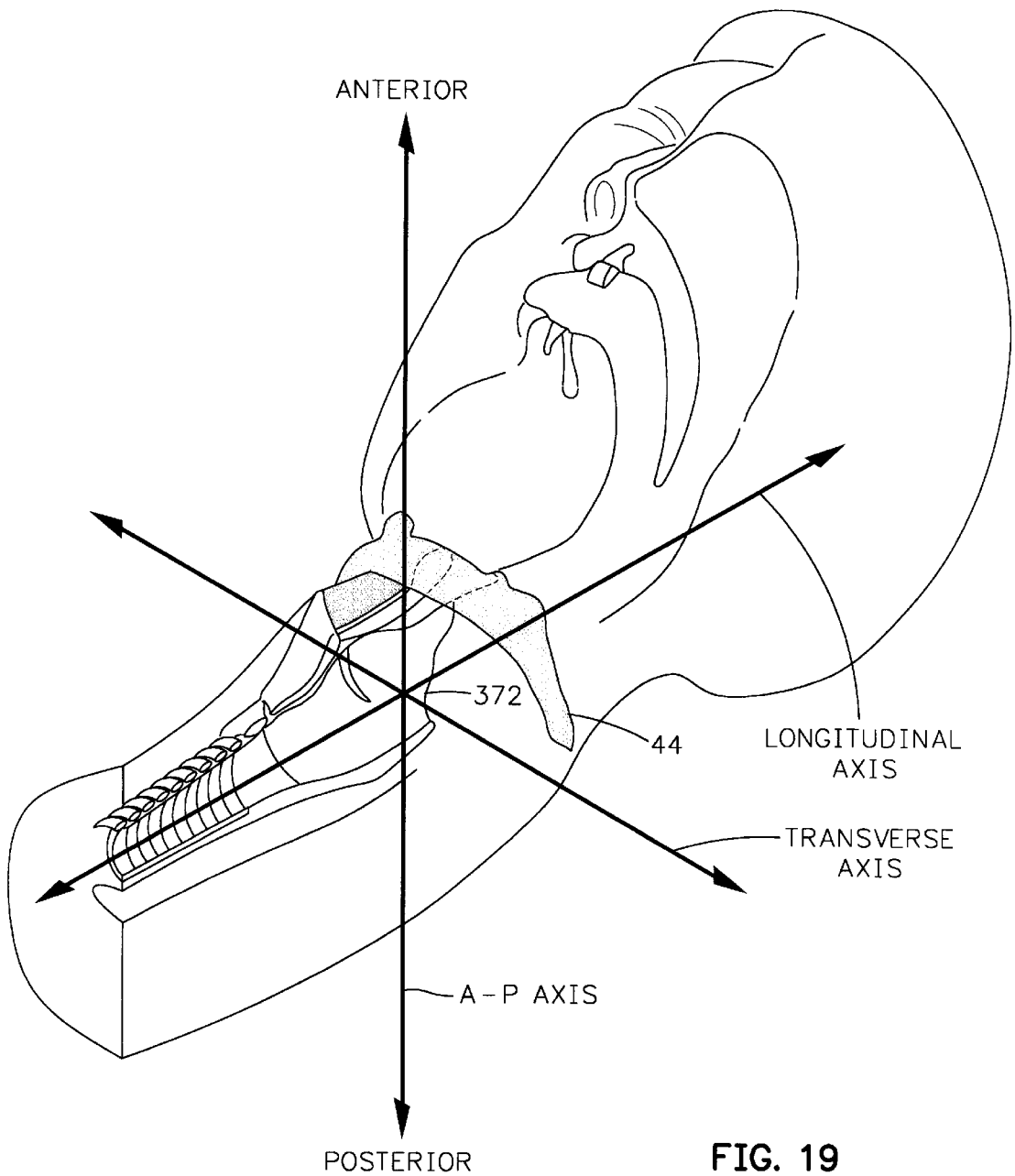
FIG. 19 is an isometric, partly schematic view of the anatomy of the throat of a patient.

Refer now to FIGS. 17 and 18 for an understanding of the operation of the fifth embodiment of our laryngeal airway device. These pictures are side views showing a side elevation section of the head and throat of a patient 338. Refer also to FIG. 19 for an understanding of the anatomical space in which the sealing member 314 must be positioned for accurately and dependably seating in the throat of a patient. (Although not shown in these illustrations, a pharyngeal blade, such as the blade 50 discussed previously, may be used to assist in the insertion of the laryngeal airway device 300).

As FIG. 17 illustrates, when the sealing member 314 of the laryngeal airway device 300 is seated against the laryngeal opening, the distal extension 317e of the anterior surface 317 is lodged in the hypopharyngeal space 349, just above the esophagus. At the same time, the proximal anterior extension 317a and the upper portion of the convex curve 317b press against the epiglottis 342, forcing it in an anterior direction toward the tongue 343, thereby stretching the ary-epiglottic folds, which create a relatively firm rim at the laryngeal inlet.

The angle that the lateral anterior portions 317c of the anterior surface 317 form with respect to the longitudinal axis 312LA have been previously described. In addition, the distal extension 317e of the anterior surface 317 is angled toward the longitudinal axis 312LA, but projected distally. This forms the tight concave curve in the anterior surface 317, at 317d. The portion of the anterior surface 317 that transitions through the concave curve 317d creates a reliable end-point to insertion of the laryngeal airway device when it firmly abuts the arytenoid cartilages 352 of the laryngeal inlet. This end point accurately positions the laryngeal airway device longitudinally, with respect to the laryngeal inlet, along or substantially parallel to the longitudinal axis shown in FIG. 19.

Assuming that the patient 338 is supine, the larynx can be expected to be resting on the posterior wall 351 of the patient's hypopharynx 349. In this case, the distal extension 317e of the anterior surface 317 is inserted between the posterior side 350 of the larynx and the posterior wall 351. Inserting the distal extension 317e between these two structures holds the laryngeal airway device 300 in place, stabilizing the device 300 to prevent movement when in use. Further, the distal extension 317e accurately positions the laryngeal device 300 along the anterior-posterior (A-P) axis (FIG. 19), which extends through, and perpendicularly to, the longitudinal axis, between the back of the patient's neck and the front of the patient's throat. The laryngeal airway device 300 is also accurately positioned in the transverse axis shown in FIG. 19 (from side-to-side of the patient's neck) by sizing the width of the anterior surface 317 and/or the support member 320 to the width of the pharynx at the level of the laryngeal inlet. In general, this width will be defined by the distance between the wings of the hyoid bone 44 (reference FIG. 19). The laryngeal airway device 300 may be slightly wider than the available space, with the provision that the material of which the pad 316 is made is compressible, which will provide a snug fit between the side walls of the pharynx.

In summary, with reference to FIGS. 17 and 19, the lateral anterior surface portions 317c, curving concavely into the distal extension 317e of the anterior surface 317, embody a means for accurately positioning the sealing member 314 with respect to the laryngeal inlet in both the longitudinal and A-P axes. Sizing the width of the anterior surface 317 to the width of the pharynx centers the device with respect to the laryngeal inlet in the transverse axis. Therefore, the sealing member 314 accurately and dependably positions itself in three axes with respect to the laryngeal inlet, when inserted blindly into the pharynx.

To ensure a dependable seal with the larynx, the laryngeal airway device 300 must be in firm contact with the laryngeal inlet. This can be difficult when the lateral rim portions of the laryngeal inlet are scalloped severely. Typical scalloping is seen in FIG. 19 in the lateral rim portion 372. The convex curve 317b is shaped to fill the scalloped rim 372. With reference to FIGS. 17, 18 and 19, such contact is provided by a thickness along the A-P axis that is sufficient to force the anterior surface 317 against the laryngeal inlet. One potential problem is that excessive thickness in the A-P dimension might make insertion of the laryngeal airway device 300 through the mouth, around the tongue 343, and into the pharynx difficult. This problem is solved in the laryngeal airway device 300 by provision of the inflatable balloon 331 that is carried on the posterior side of the air tube 312. As shown in FIG. 17, the laryngeal airway device 300 is inserted to the pharynx with the balloon 331 deflated, reducing the A-P thickness for insertion. When the anterior surface 317 is properly positioned with respect to the larynx, the balloon 331 is inflated, thereby elevating the laryngeal airway device 300 off of the posterior pharyngeal wall 351 and forcing it anteriorly against the laryngeal inlet and epiglottis 342. The balloon 331 is inflated by way of a tube 333 having at its distal a fitting 334 through which it pressurized air may be introduced for inflating the balloon 331. Inflation of the balloon and rotation of the sealing member 314 anteriorly against the epiglottis 342 are shown in FIG. 18. The anterior rotation of the sealing member 314 by inflation of the balloon 331 against the epiglottis is evidenced by a slight bulge 360 in the neck of the patient 338. When the sealing member 314 is seated in the laryngeal opening, the sigmoid shape of the anterior surface 317, particularly in the convex curve portion 317b follows the scalloping in the lateral edges of the laryngeal inlet, which enhances the seal formed between the sealing portion 314 and the laryngeal inlet.

Figure 20:
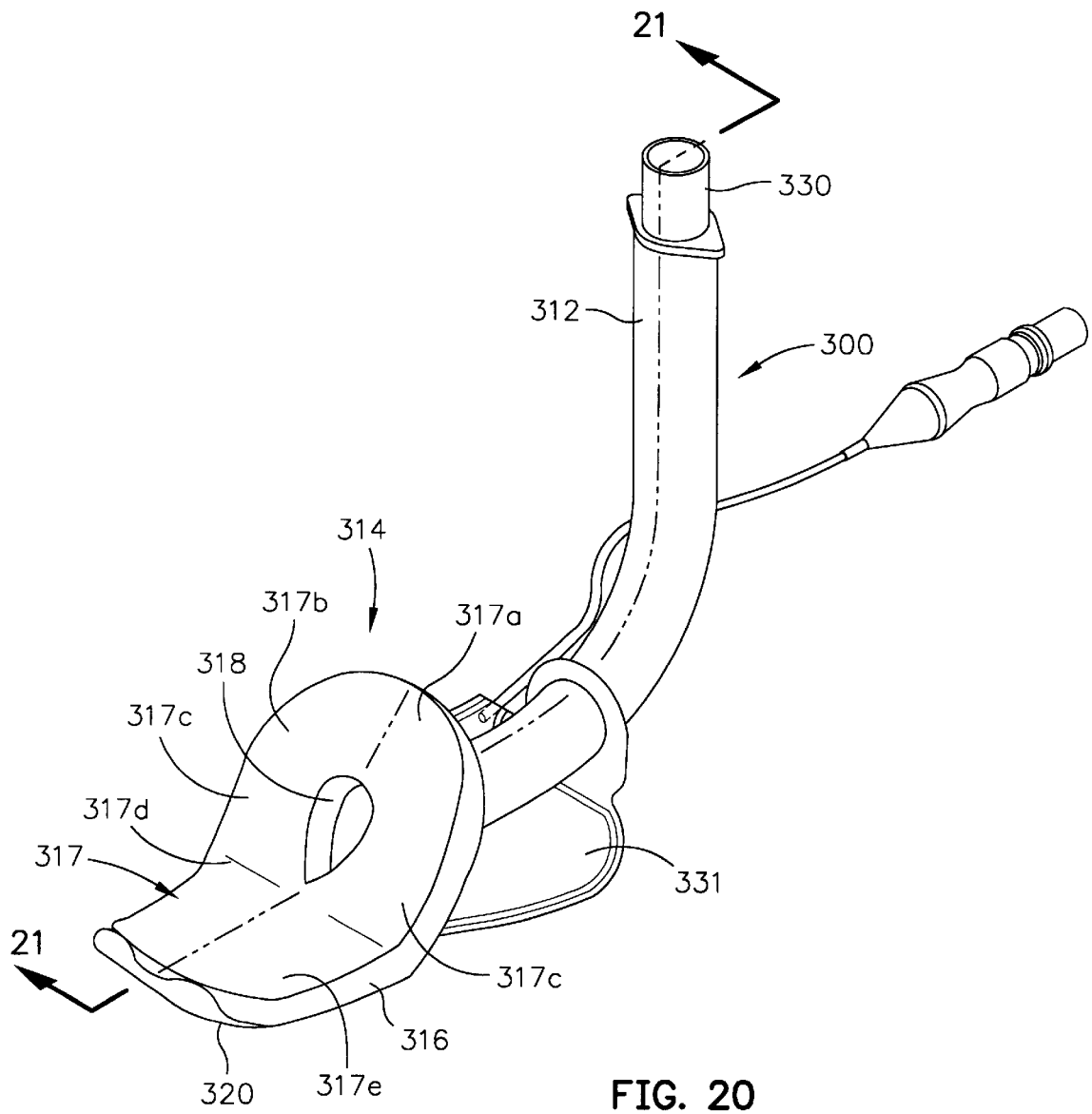
FIG. 20 is an isometric view of an optional form of the fifth embodiment.
Figure 21:
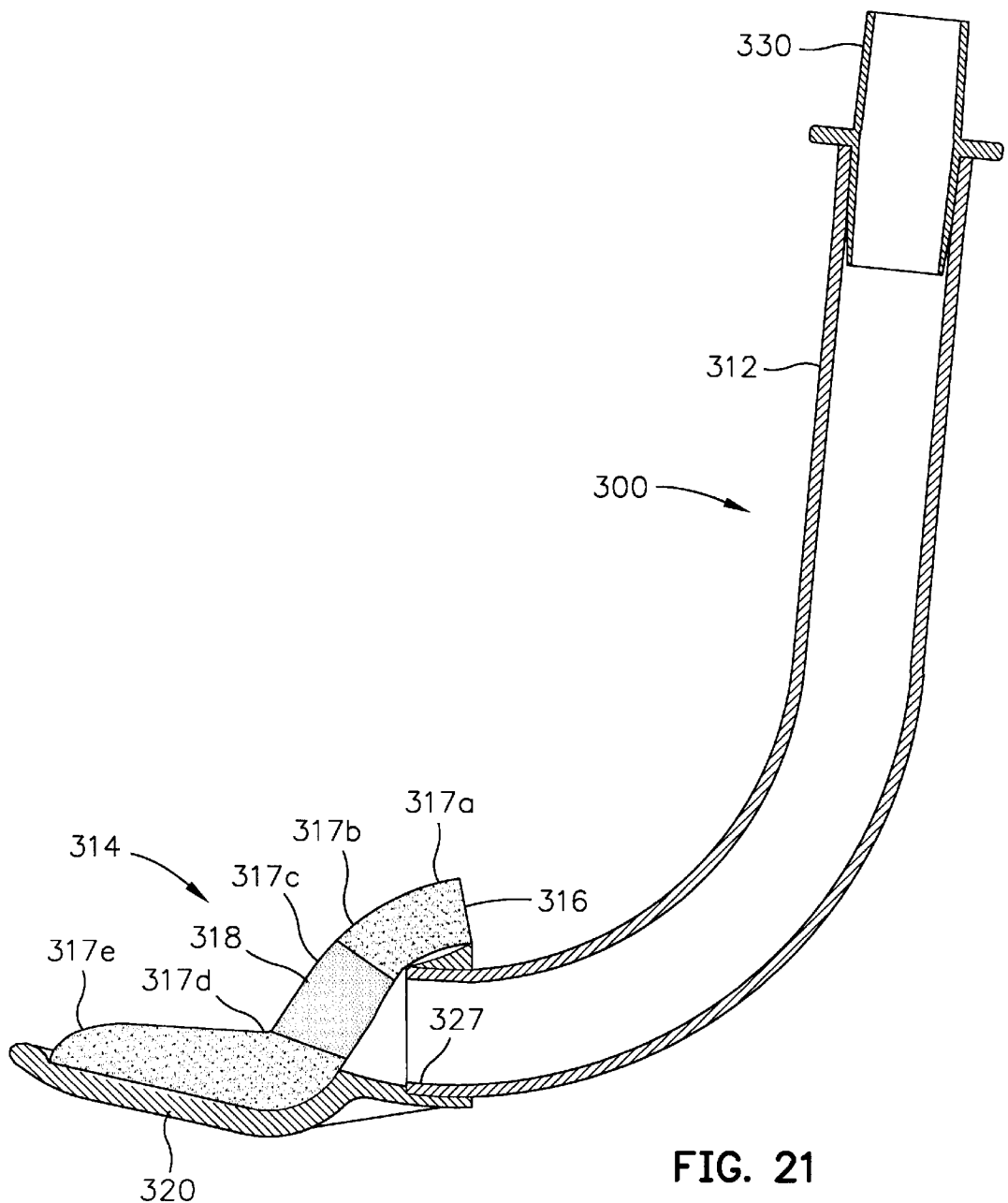
FIG. 21 is a side sectional view of the optional form of the fifth embodiment.

FIGS. 20 and 21 illustrate an optional variation of the fifth embodiment in which the sleeve 323 is omitted from the support member 320. As these figures show, even when the sleeve 323 is omitted, the anterior surface 317 of the pad 316 of the sealing member 314 has the surface features 317a, 317b, 317c, 317d, 317e that impose a sigmoid shape on the anterior surface 317.

Provision or omission of the sleeve 323 depends upon clinical and manufacturing considerations. The support member 320 is preferably a molded plastic piece in which the sleeve 323 can be included, or omitted.

Further, the fifth embodiment of the laryngeal airway device 300 may be adapted to include the integral perforations of previously-described embodiments that would enable the device 300 to be used as a channel for intubation which could be stripped away from an in-place endotracheal tube, if desired.

While our invention has been illustrated and described with reference to particular embodiments, it will be understood by those skilled in the art that various changes and modifications can be made to those embodiments, and other embodiments can be provided, without departing from the scope of the invention, which is limited only by the following claims.

What is claimed is:

1. A laryngeal airway device for ventilation of the airway of a person, comprising:
    an air tube with two ends;
    a sealing member mounted near a first end of the air tube;
    a passageway in the sealing member in communication with the air tube;
    the sealing member including a compressible pad with a contoured anterior surface and a support member posterior to the pad; and
    at least one hole in the pad which opens through the anterior surface to the passageway.

2. The laryngeal airway device of claim 1, wherein the anterior surface has a sigmoid contour.

3. The laryngeal airway device of claim 2, wherein the support member includes a collar disposed in the passageway and extending through the hole, and the first end of the air tube is received in one end of the collar.

4. The laryngeal airway device of claim 3, wherein the cross section of the collar tapers from the one end to a second end.

5. The laryngeal airway device of claim 2, wherein the sigmoid contour includes:
    an anterior extension of the anterior surface;
    lateral anterior surface portions on sides of the hole;
    a distal anterior surface extension;
    a convexly curved anterior surface portion that joins the anterior extension and the lateral anterior surface portions; and
    a concavely curved anterior surface portion that joins the lateral anterior surface portions with the distal anterior surface extension.

6. The laryngeal airway device of claim 5, wherein the lateral anterior surface portions form an angle with a longitudinal axis extending from the first end of the air tube, and the angle is in the range of 30° to 90°.

7. The laryngeal airway device of claim 6, wherein the angle is preferably 55°.

8. The laryngeal airway device of claim 1 wherein the air tube comprises a flexible tube.

9. The laryngeal airway device of claim 8 wherein the flexible tube is made of polymeric plastic.

10. The laryngeal airway device of claim 8 wherein the flexible tube is made of polymeric rubber.

11. The laryngeal airway device of claim 8 wherein the flexible tube includes at least one longitudinal section which creates a line of weakness in a wall of the tube.

12. The laryngeal airway device of claim 11 wherein the flexible tube includes two longitudinal sections which form a removable strip on the flexible tube.

13. The laryngeal airway device of claim 12 wherein the removable strip is on an anterior wall of the flexible tube and includes a tab.

14. The laryngeal airway device of claim 1 wherein the support member includes an elbow.

15. The laryngeal airway device of claim 1 wherein the air tube is a flexible molded part with a removable strip of material.

16. The laryngeal airway device of claim 15 wherein the material forming a wall of the air tube is weakened along a line to create a seam.

17. The laryngeal airway device of claim 15 wherein the material forming a wall of the air channel is perforated in two parallel lines to form a tear strip.

18. The laryngeal airway device of claim 15 further including material forming a wall bonded to the molded part.

19. The laryngeal airway device of claim 1, wherein the support member has an anterior surface and a slot, a posterior surface of the pad being disposed against the anterior surface of the support member over the slot thereby to form the passageway.

20. The laryngeal airway device of claim 19, wherein the air tube includes at least one section extending along its length which creates a line of weakness in a wall of the tube and the pad includes a line of weakness over the slot in alignment with the at least one section.

21. The laryngeal airway device of claim 19, further including a posterior pad that is bonded to a posterior surface of the support member.

22. The laryngeal airway device of claim 1, wherein the support member is compliant, but stiffer than the pad.

23. The laryngeal airway device of claim 22, wherein the pad comprises a first soft, compliant material and the support member comprises a second soft, compliant material, the material of the pad being softer and more compliant than the material of the support member.

24. The laryngeal airway device of claim 1, further including an inflatable member mounted posteriorly on the sealing member.

25. A combination to facilitate lung ventilation in a person, comprising:
   a laryngeal airway device with a proximal air channel and a distal sealing member adapted to seat in the pharynx of the person and to sealably engage the inlet of the larynx of the person, the sealing member including a passageway to the air channel, a compressible pad with a contoured anterior surface, a support member posterior to the pad, and at least one hole in the pad which opens through the anterior surface to the passageway;
   a pharyngeal blade for introducing the sealing member into the pharynx; and,
   attachment means for attaching the pharyngeal blade to the laryngeal airway device.

26. The combination of claim 25 wherein the pharyngeal blade includes at least one hole.

27. The combination of claim 25 wherein the attachment means is for attachment of the pharyngeal blade to the sealing member.

28. The combination of claim 27 wherein the attachment of the pharyngeal blade to the sealing member compresses at least a portion of the anterior surface.

29. The combination of claim 27 wherein the distal tip portion of the pharyngeal blade extends beyond the distal margin of the laryngeal airway device when attached to the laryngeal airway device.

30. The combination of claim 25, wherein the pharyngeal blade comprises an elongate strip of material for insertion through the oral cavity of the person and into the lower pharynx of the person.

31. A laryngeal airway device for ventilation of the airway of a person, composing:
   an air tube;
   a sealing member attached to a distal end of the air tube;
   a passageway in the sealing member;
   the sealing member including a compressible pad with a contoured anterior surface adapted to intrude into the laryngeal inlet of the person;
   at least one hole which opens between the anterior surface and the passageway; and
   said air tube including a proximal end, and a distal end in communication with the passageway.

32. The laryngeal airway device of claim 31, further including an inflatable member mounted posteriorly on the sealing member.

33. The laryngeal airway device of claim 31, wherein the sealing member includes:
   a support member;
   the pad being attached to the support member.

34. The laryngeal airway device of claim 33, wherein the support member includes a collar disposed in the passageway and extending through the hole, and the distal end of the tube is received in one end of the collar.

35. The laryngeal airway device of claim 34, wherein the cross section of the collar tapers from the one end to a second end.

36. A method of managing an airway of a person using a laryngeal airway device having a proximal air channel and a distal sealing member having a contoured anterior surface, a hole through the anterior surface and the sealing member in communication with a distal end of the air channel, comprising the steps of:
   advancing the laryngeal airway device, distal sealing member first along the tongue of the person until the sealing member lodges in hypopharyngeal space of the person;
   the contoured anterior surface projecting into and forming a seal with the laryngeal inlet of the person;
   the hole being positioned at the laryngeal inlet; and
   ventilating the airway and lungs of the person through the proximal air channel.

* * * * *

UNITED STATES PATENT AND TRADEMARK OFFICE
CERTIFICATE OF CORRECTION

PATENT NO.   : 6,070,581
DATED        : June 6, 2000
INVENTOR(S)  : Augustine et al It is certified that error appears in the above-indentified patent and that said Letters Patent is hereby corrected as shown below:

On the title page, insert

[56]     References Cited 4,509,514   04/85   Brain   128/207.15
   5,241,956   09/93   Brain   128/207.15
   5,303,697   04/94   Brain   128/200.26
   5,355,879   10/94   Brain   128/207.15

Signed and Sealed this

Third Day of April, 2001

*Attest:*

NICHOLAS P. GODICI

*Attesting Officer*   Acting Director of the United States Patent and Trademark Office